United States Patent [19]

Leanza et al.

[11] Patent Number: 4,748,162

[45] Date of Patent: * May 31, 1988

[54] 6-SUBSTITUTED-2-CARBAMINIDOYL-PEN-2-EM-3-CARBOXYLIC ACIDS

[75] Inventors: William J. Leanza, Berkeley Heights; Burton G. Christensen, Cliffside Park; Frank P. DiNinno, Old Bridge; Ronald W. Ratcliffe, Matawan, all of N.J.

[73] Assignee: Merck & Co., Inc., Rahway, N.J.

[*] Notice: The portion of the term of this patent subsequent to Mar. 17, 2004 has been disclaimed.

[21] Appl. No.: 605,338

[22] Filed: Apr. 30, 1984

Related U.S. Application Data

[63] Continuation of Ser. No. 353,453, Mar. 1, 1982, abandoned.

[51] Int. Cl.$^4$ .................. C07D 499/00; A61K 31/425
[52] U.S. Cl. ..................................... 514/192; 514/195; 540/310
[58] Field of Search ................. 260/245.2 R, 245.2 T; 424/270, 271; 540/310; 514/192, 195

[56] References Cited

U.S. PATENT DOCUMENTS 4,395,418  7/1983  Ohri et al. ................... 260/245.2 R
4,517,124  5/1985  Broom ......................... 260/245.2 R

FOREIGN PATENT DOCUMENTS 2074563A  11/1981  United Kingdom .

Primary Examiner—Nicholas S. Rizzo

Attorney, Agent, or Firm—Raymond M. Speer; Hesna J. Pfeiffer

[57] ABSTRACT

Disclosed are 6-substituted-2-carbamimidoyl-pen-2-em-3-carboxylic acids (I) having the representative structure:

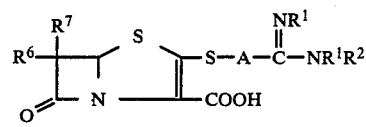

wherein $R^6$, and $R^7$ are, inter alia, independently selected from the group consisting of hydrogen, alkyl, alkoxyl, halo, OH, COOH, alkenyl, aryl and aralkyl; A is a direct, single bond connecting the indicated S and C atoms, or A is a cyclic or acyclic connecting group selected, inter alia, from alkyl, cycloalkyl, aryl, heteroaryl, heteroalkyl; $R^1$ and $R^2$, which define the carbamimidoyl function, are, inter alia, independently selected from hydrogen, alkyl, aryl; additionally, said carbamimidoyl is characterized by cyclic structures achieved by the joinder of the two nitrogen atoms via their substituents and by their joinder to connecting group A; additionally, "carbamimidiums" are disclosed by quarternization of one of the nitrogen atoms of said carbamimidoyl. Such compounds as well as their pharmaceutically acceptable salt, ester and amide derivatives are useful as antibiotics. Also disclosed are processes for the preparation of such compounds; pharmaceutical compositions comprising such compounds; and methods of treatment comprising administering such compounds and compositions when an antibiotic effect is indicated.

25 Claims, No Drawings

6-SUBSTITUTED-2-CARBAMINIDOYL-PEN-2-EM-3-CARBOXYLIC ACIDS

This is a continuation of application Ser. No. 353,453, filed Mar. 1, 1982, now abandoned.

BACKGROUND OF THE INVENTION

This invention relates to 6-substituted-2-carbamimidoyl-pen-2-em-3-carboxylic acids (I) and the pharmaceutically acceptable salt, ester and amide derivatives thereof which are useful as antibiotics:

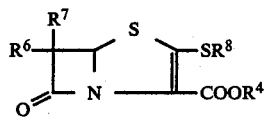

wherein $R^6$ and $R^7$ are independently selected from the group consisting of: hydrogen; substituted and unsubstituted: alkyl, alkoxyl, alkenyl, and alkynyl, having from 1–10 carbon atoms; halo (especially chloro and fluoro); hydroxyl; carboxyl; cycloalkyl, cycloalkylalkyl and alkylcycloalkyl, having 3–6 carbon atoms in the cycloalkyl ring and 1–6 carbon atoms in the alkyl moieties; aryl such as phenyl; aralkyl, aralkenyl, and aralkynyl wherein the aryl moiety is phenyl and the aliphatic portion has 1–6 carbon atoms; heteroaryl, heteroaralkyl, heteroalkyl, heterocyclyl and heterocyclylalkyl; wherein the heteroatom or atoms are selected from O, N and S; wherein the substituent or substituents on $R^6$ and $R^7$ are independently selected from chloro, fluoro, carboxyl, amino, $R°NH$, $R°_2N$ ($R°$ is $C_{1-6}$ alkyl); bromo, hydroxy, and alkoxyl having 1–6 carbon atoms; additionally $R^6$ and $R^7$ may be joined to form, together with the carbon atom to which they are attached, a cyclicalkyl having 3–6 carbon atoms.

$R^8$ is generically defined to be a "carbamimidoyl", which may be defined by the following structures:

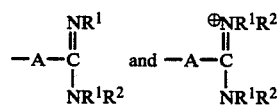

wherein A, the cyclic or acylic connecting group, and $R^1$ and $R^2$ are defined below. The definition of $R^8$ also embraces cyclic structures, which may be generically represented, for example, thusly:

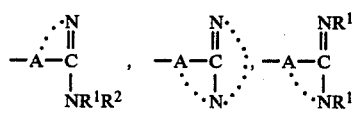

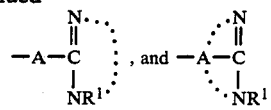

wherein the dotted lines indicate that the nitrogen atoms of the so-called carbamimidoyl function may participate in the formation of the cyclic structures indicated above. Representative specific embodiments for $R^8$ (as well as $R^6$ $R^7$) follow, but, in the generic sense, the components: $R^1$, $R^2$ and A which comprise $R^8$ are defined, thusly:

A, the cyclic or acyclic connector, is selected from the group consisting of alkyl, alkenyl, and alkynyl having 1–10 carbon atoms which may be interrupted by a hetero atom selected from O, S or N, or by a ring such as phenyl, cycloalkyl, cycloalkenyl, heterocyclyl or heteroaryl wherein such cyclic interruptions comprise 3–6 ring atoms selected from C, O, S and N; cycloalkyl, cycloalkenyl having 3–6 carbon atoms; heterocyclyl; heteroaryl; and phenyl; A also represents a direct, single bond connecting the indicated S and C atoms.

$R^1$ and $R^2$ are independently selected from hydrogen and the previously defined values for the group A, such as: alkyl, aryl, cycloalkyl, heteroarlkyl, alkylaryl, alkylarylalkyl, and heterocyclyl and heteroaryl.

$R^4$ is hydrogen, a removable protecting group, a synthetically useful salt moiety, or a pharmaceutically acceptable salt or ester moiety.

It should be noted that the final products of this invention (I) can exist in either neutral or zwitterionic (internal salt) forms. In the zwitterionic form, the basic function is protonated and positively charged and the carboxyl group is deprotonated and negatively charged. The zwitterionic form is the predominant species under most conditions and is in equilibrium with a minor amount of the uncharged, neutral species. The equilibrium process is conveniently visualized as an internal acid-base neutralization. The neutral and zwitterionic forms are shown below.

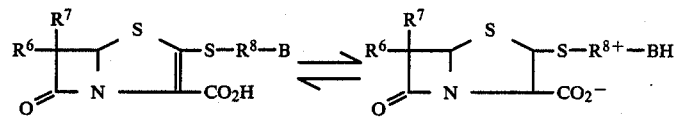

wherein B is the carbamimidoyl group.

Further, the final products of this invention I wherein $R^8$ contains a positively charged quaternary nitrogen function such as the "carbamimidinium" can exist as zwitterionic (internal salt) forms or as external salt forms. The preferred form of this product group is the zwitterionic or internal salt form. These forms are shown below:

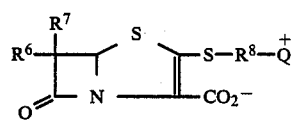

Zwitterionic (internal salt) Form

-continued

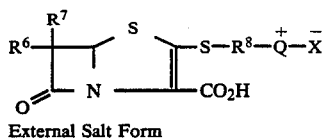
External Salt Form wherein Q represents the quaterized nitrogen group, and wherein X is a pharmaceutically acceptable anion such as those listed in U.S. Pat. No. 4,194,047, issued 3/18/80, which is incorporated herein by reference.

This invention also relates to the carboxyl derivatives of I which are antibiotics and which may be represented by the following generic structure (I):

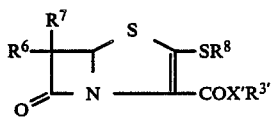

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens which representatively include both Gram positive bacteria such as *S. aureus, Strep. pyogenes,* and *B. subtilis,* and Gram negative bacteria such as *E. coli,* Pseudomonas, *Proteus morganii,* Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

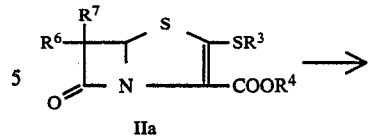

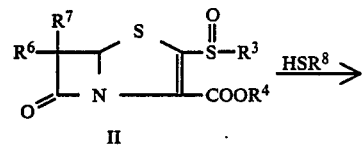

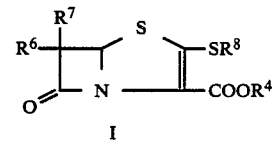

Transformation IIa to II

Relative to the above reaction scheme, there is no undue criticality as to the precise identity of the oxidizing agent. Suitable oxidizing agents include peracids such as m-chloroperbenzoic acid and peracetic acid. Other representative oxidizing agents include potassium permanganate, hydrogen peroxide, sodium meta periodate, t-butyl hydrogen peroxide, dichloroiodobenzene, sulfuryl chloride with wet silica gel, sodium hypochlorite, and ozone, for example. Typically, 1.0 eq. to a slight excess of oxidizing reagent is employed. There is no criticality as to reaction solvent—any solvent being acceptable which is inert or substantially inert during the course of reaction and which effectively solubilizes the starting material IIa. Representative examples of suitable solvents for the oxidation include tetrahydofuran, methylenechloride, dimethylformamide, methanol and water. Typically, the reaction is conducted at a temperature of from about −78° to 50° C., for from a few minutes to several hours. As mentioned above, starting materials IIa are known.

Transformation II to I

The transformation II to I is accomplished by treating II with the reagent of choice, $HSR^8$, in the presence of a base. Suitable bases for this reaction include N-heterocycles, amines, trialkylamines, and inorganic bases, such as, diisopropylethylamine, triethylamine, N-methylpiperidine, potassium carbonate, and sodium bicarbonate. In the alternative, the reaction may proceed without the addition of base when the $HSR^8$ reagent is taken as its salt: $M^+ {}^-SR^8$ wherein $M^+$ is $Li^+$, $Na^+$, $K^+$ or $R^4N^+$, for example: wherein R is independently chosen from: alkyl having 1-16 carbon atoms or aralkyl having 7-12 carbon atoms; for example: methyl, ethyl, butyl, benzyl, hexadecyl or the like. Typically, the reaction is run in a solvent such as dimethylformamide, acetonitrile, dimethylsulfoxide, water or mixtures thereof, at a temperature of from −50° to 30° C. (preferably in the rang from −30° to 15° C.) for from 1 min to 24 hours. Reactions are conducted in water as the solvent or cosolvent can be kept in the pH 7-8.5 range with a suitable buffer.

Preferably, the reaction II to I is conducted in the presence of a sulfenic acid trap. The sulfenic acid trap may be accomplished by using excess $HSR^8$ or, in the alternative, using relatively, non-reactive, mercaptans such as trityl mercaptan, olefins such as: cyclohexene, isobutylene, dihydropyran; phosphines such as triphenyl phosphine, tributylphosphine, or the like, may also be employed.

Relative to starting material II concurrently filed, commonly assigned U.S. patent application Ser Nos. 353,451, (filed Mar. 1, 1982) and 353,452 (filed Mar. 1, 1982), [respectively] are incorporated herein by reference to the extent that they define II and its manner of preparation:

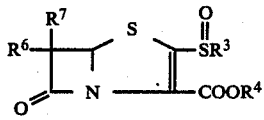

In brief, relative to starting material II, $R^6$, $R^7$ and $R^4$ are as defined, and $R^3$ is alkyl, aralkyl, or cycloalkyl. They are prepared from the corresponding 2-$SR^3$ species (IIa) by oxidation. The 2-$SR^3$ starting penems are known. See U.S. Pat. No. 4,260,618 (issued 4-7-81); U.K. Patent Application No. G.B. 201 3674 A (published Aug. 15, 1979); and U.K. Patent Application No. G.B. 2042520H (published Sept. 24, 1980), which documents are incorporated herein by reference.

$HSR^8$ REAGENTS

Relative to the foregoing description of the invention, suitable carbamimidoyl and carbamimidinium mercaptans $HSR^8$ which are utilized in the transformation II to I are listed below. Wherein $R^8$ is:

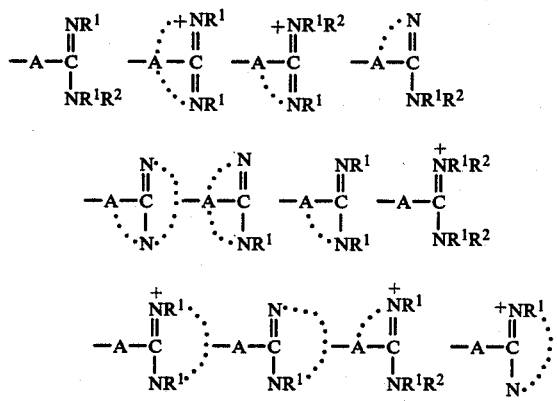

and wherein $R^1$ and $R^2$ are as initially defined under $R^8$; the two nitrogen atoms demonstrated in the above structure may participate in cyclic structures which are indicated by the dotted lines; A is a connecting group between the sulfur atom and carbamimidoyl function. It should be noted that while not all conical forms of $R^8$ are reproduced herein, the foregoing list is representative and constitutes together with the associated text a definition of the "carbamimidoyl" group of the present invention.

$R^1$ and $R^2$ are independently selected from the group consisting of hydrogen; substituted and unsubstituted: straight and branched alkyl having from 1 to 6 carbon atoms; cycloalkyl having 3 to 6 carbon atoms; cycloalkylalkyl wherein the cycloalkyl moiety comprises 3 to 6 carbon atoms and the alkyl moiety comprises 1 to 6 carbon atoms; alkylcycloalkyl wherein the alkyl moiety comprises 1 to 6 carbon atoms and the cycloalkyl moiety comprises 3 to 6 carbon atoms; aryl such as phenyl; arylalkyl such as benzyl; heterocyclyl (saturated and unsaturated) comprising mono- and bicyclic structures having from 5 to 10 ring atoms, wherein one or more of the heteroatoms is selected from oxygen, nitrogen, or sulfur, such as thiophene, imidazole, tetrazolyl, furyl, pyridine; heterocyclylalkyl groups which comprise the immediately preceding heterocyclyl moieties and the alkyl moiety comprises 1 to 6 carbon atoms. The substituent or substituents relative to the above-named radicals comprising $R^1$ and $R^2$ are selected from the group consisting of amino, hydroxy, cyano, carboxyl, nitro, chloro, bromo, fluoro, alkoxy, and alkylthio having from 1 to 6 carbon atoms, mercapto, perhaloalkyl having 1 to 3 carbon atoms, guanidino, amidino, sulfamoyl. When located on the same nitrogen atom, the substituents $R^1$ and $R^2$ can be joined to form a cyclic group comprising 3-8 atoms. The resulting ring can contain additional O, S or N atoms. For example, —$NR^1R_2$ can be taken as morpholino, pyrrolidino, piperidino, azetidinyl or the like.

Particularly preferred groups under the definition of $R^1/R^2$ are: hydrogen; substituted and unsubstituted: straight and branched loweralkyl having from 1 to 6 carbon atoms; cycloalkyl having from 3 to 6 carbon atoms, cycloalkylalkyl wherein the cycloalkyl moiety comprises 3 to 6 carbon atoms and the alkyl moiety comprises 1 to 6 carbon atoms; aryl such as phenyl, arylalkyl such as benzyl; the substituents on the above-named radicals are selected from fluoro, hydroxy, mercapto, alkoxy and alkylthio having from 1 to 3 carbon atoms.

In defining the bivalent, cyclic or acyclic connector group "A", it is to be noted that the recited radicals of definition are to be read both left to right and right to left. Thus, the preferred connecting groups "A" are selected from: substituted and unsubstituted: loweralkyl having from 1-6 carbon atoms; cycloalkyl having from 3-10 atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; loweralkenyl having from 2-10 carbon atoms, cycloalkenyl having from 3 to 10 carbon atoms, cycloalkenylalkyl wherein the cycloalkenyl moiety comprises 3 to 10 carbon atoms; and the alkyl moiety comprises 1 to 6 carbon atoms; alkynyl having from 2 to 10 carbon atoms; aryl such as phenyl and naphthyl; arylalkyl and alkylaryl such as benzyl, phenethyl and the like; heteroalkyl, alkylheteroalkyl, arylheteroarlky and alkylheteroaryl wherein the heter atoms are selected from the group of sulfur, oxygen and nitrogen, and the alkyl moiety has 1 to 6 carbon atoms, and the aryl moiety is phenyl; heterocyclyl (saturated and unsaturated) comprising mono- and bicyclic structures having 5 to 10 ring atoms wherein one or more of the hetero atoms is selected from oxygen, nitrogen, or sulphur such as thiophene, imidazole, pyridine, furyl and the like; heterocyclylalkyl wherein the heterocyclyl moiety comprises from 3 to 10 atoms and the alkyl moiety comprises from 1 to 6 atoms; the substituent (or substituents) relative to the above-named radicals are selected from the group consisting of amino, hydroxyl, cyano, carboxyl, nitro, chloro, bromo, fluoro, alkoxy having from 1 to 6 carbon atoms, mercapto, perhaloloweralkyl such as trifluoromethyl and alkylthio having from 1-6 carbon atoms.

A particularly preferred class of connecting groups "A" are selected from: a single bond connecting the sulfur and carbamimidoyl function; substituted and unsubstituted: straight and branched loweralkyl having from 1 to 6 carbon atoms, cycloalkyl having from 3 to 6 carbon atoms; phenyl; heterocyclyl such as thiophene, imidazole, pyridine, and furane; alkylheteroalkyl wherein alkyl moiety comprises 1 to 3 carbon atoms and the hetero atoms are sulfur, oxygen and nitrogen; the substituents relative to the above-named radicals are: amino, hydroxyl, chloro, bromo, fluoro, cyano, carboxyl alkoxy having from 1 to 3 carbon atoms, mercapto, trifluoromethyl, and alkylthio having from 1 to 3 carbon atoms.

Representative examples of such preferred —SR[8] groups (represented as HSR[8]) are:

EXAMPLES

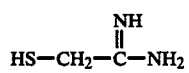

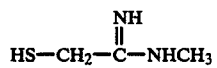

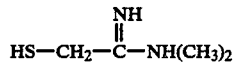

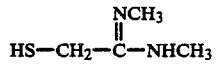

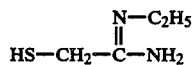

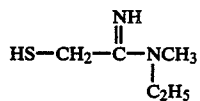

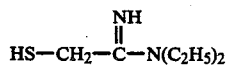

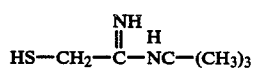

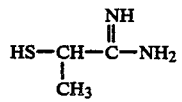

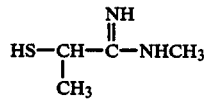

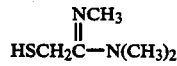

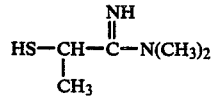

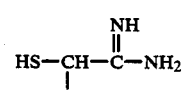

-continued

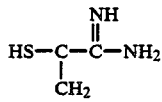

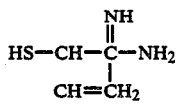

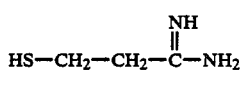

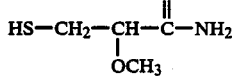

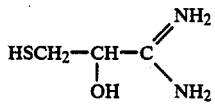

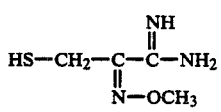

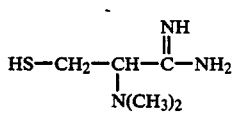

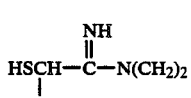

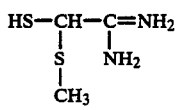

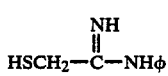

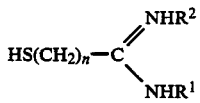

n = 2-5, R[2] = H, CH$_3$
R[1] = H, CH$_3$

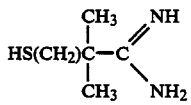

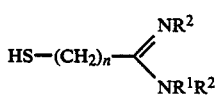

n = 2-5, R[1], R[2] = H, CH$_3$

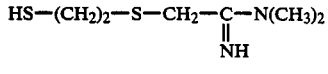

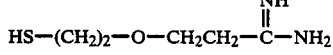

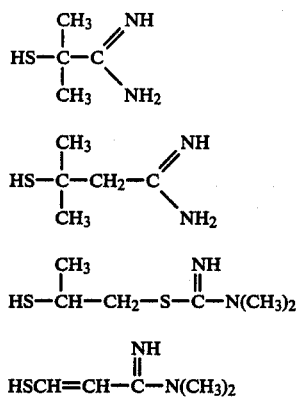
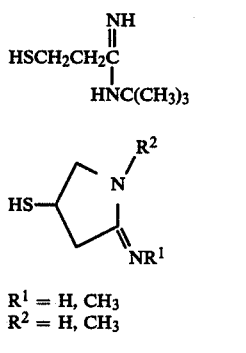
R¹ = H, CH₃
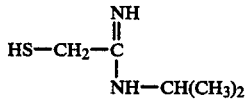
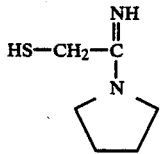
R¹ = H, CH₃
R² = H, CH₃
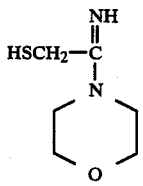
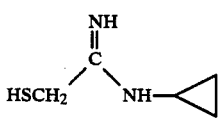
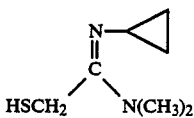
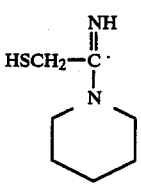
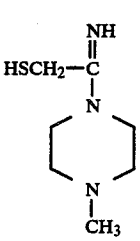
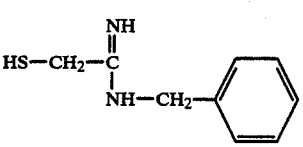
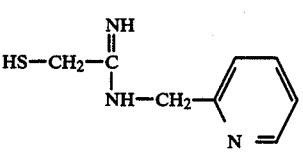
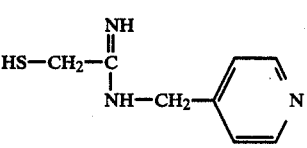
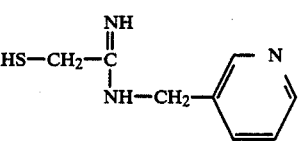
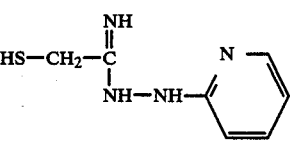
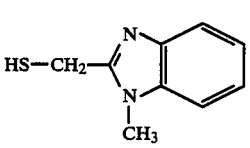
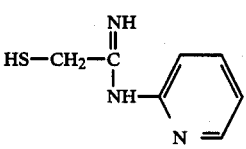

-continued
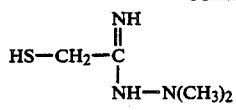
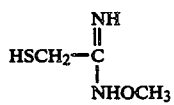
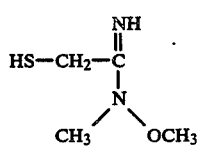
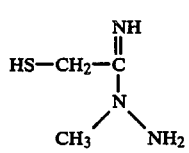
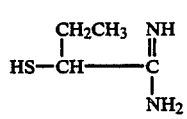
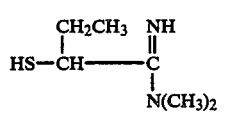
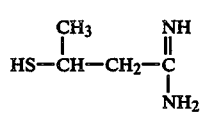
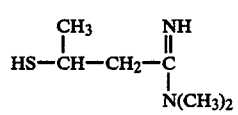
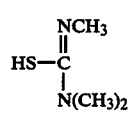
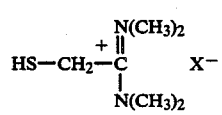
X = any compatible anion
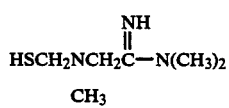
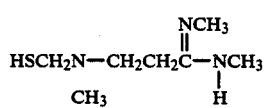
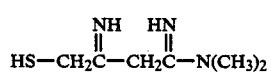
-continued
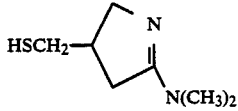
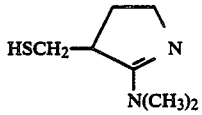
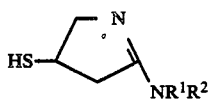
$R^1$ = H, $CH_3$
$R^2$ = H, $CH_3$
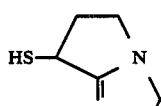
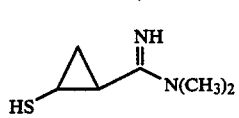
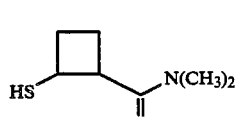
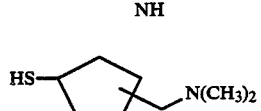
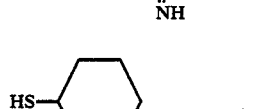
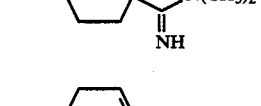
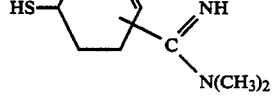
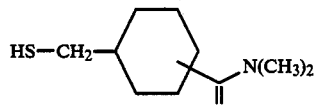
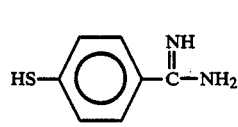
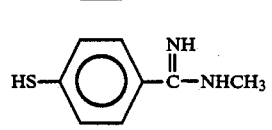

-continued
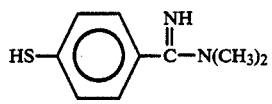
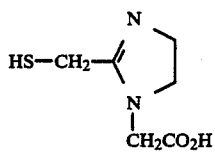
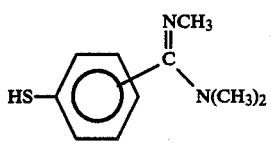
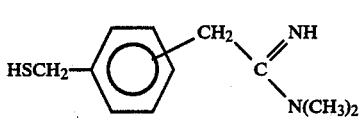
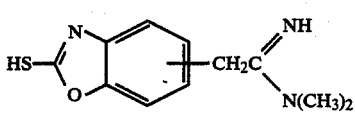
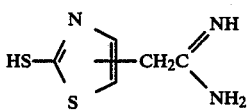
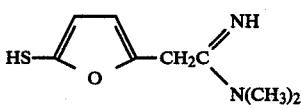
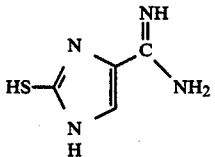
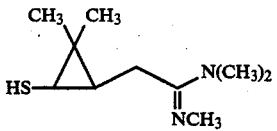
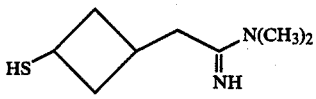
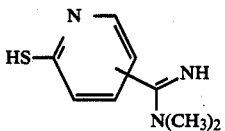
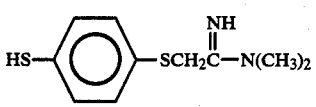
-continued
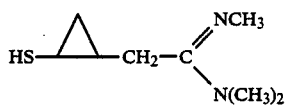
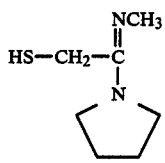
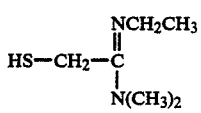
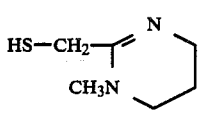
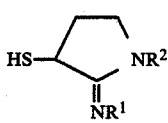
$R^1$ = H, $CH_3$
$R^2$ = H, $CH_3$
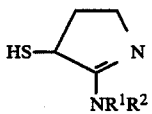
$R^1$ = H, $CH_3$
$R^2$ = H, $CH_3$
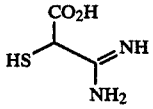
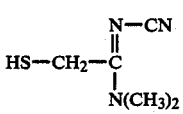
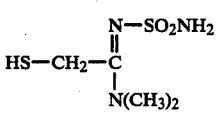
$R^1$ = $CH_3$
$R^2$ = $CH_3$, $N(CH_3)_2$, $OCH_3$
$R^3$ = H, $CH_3$
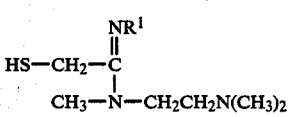
$R^1$ = H, $CH_3$ -continued

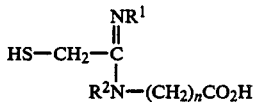

R¹ = H, CH₃
R² = H, CH₃
n = 1 or 2

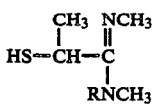

R = H, CH₃

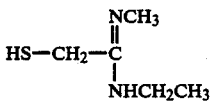

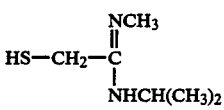

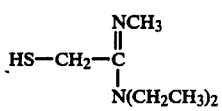

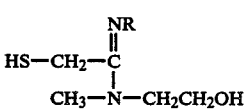

R = CH₂CH₃, CH₃, H

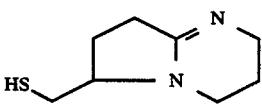

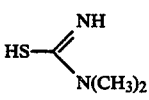

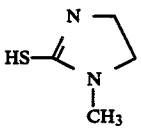

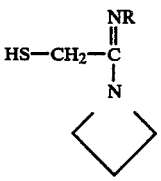

R = H, CH₃

It is recognized that SR⁸ side chains in which the R⁸ group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved —SR⁸ side chains.

As noted above, the compounds of the present invention may also generally be represented by the following structural formula:

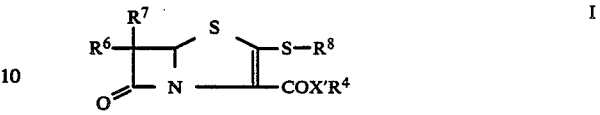

wherein X' is oxygen, sulfur or NR' (R' is hydrogen or loweralkyl having from 1 to 6 carbon atoms); and R⁴ is hydrogen, or, inter alia, is representatively selected to provide the pharmaceutically acceptable salt, ester, anhydride (R⁴ is acyl), and amide moieties known in the bicyclic β-lactam antibiotic art; R⁴ may also be a readily removable blocking group or a synthetic useful salt moiety. A synthetically useful salt moiety consists of a highly lipophilic carboxylate cation which imparts organic solubility to the molecule. This type of carboxylate derivative allows reactions, and particularly the displacement reaction of II to I, to be conducted in an organic solvent. Representative examples of such highly lipophilic carboxylate cations R⁴ are ammonium salts R₄ᵃN⁺ wherein Rᵃ are independently selected from 1–16 carbon alkyl groups or 7 to 10 carbon aralkyl groups. A particularly useful example of this type is the N,N-dimethyl-N-benzyl-N-hexadecyl ammonium salt.

Identification of the Radical —COX'R⁴

In the generic representation of the compounds of the present invention (I, above), the radical represented by —COX'R⁴ is, inter alia, —COOH (X' is oxygen and R⁴ is hydrogen) and all radicals known to be effective as pharmaceutically acceptable ester, anhydride (R⁴ is acyl) and amide radicals in the bicyclic β-lactam antibiotic art, such as the cephalosporins and penicillins and nuclear analogues thereof.

Suitable, but representative, blocking esters R⁴ (X'=O) include those selected from the following list which is representative:

(i) R⁴=CRᵃRᵇRᶜ wherein at least one of Rᵃ, Rᵇ, and Rᶜ is an electron-donor, e.g., p-methoxyphenyl. The remaining Rᵃ, Rᵇ and Rᶜ groups may be hydrogen or organic substituting groups. Suitable ester groups of this type include p-methoxybenzyloxycarbonyl.

(ii) R⁴=CRᵃRᵇRᶜ wherein at least one of Rᵃ, Rᵇ and Rᶜ is an electron-attracting group, e.g., p-nitrophenyl, trichloromethyl, and o-nitrophenyl. Suitable esters of this type include p-nitrobenzyloxycarbonyl, 2,2,2-trichloroethoxycarbonyl, and acetonyloxycarbonyl.

(iii) R⁴=CRᵃRᵇRᶜ wherein at least two of Rᵃ, Rᵇ and Rᶜ are hydrocarbon such as alkyl, e.g., methyl or ethyl, or aryl, e.g., phenyl and the remaiing Rᵃ, Rᵇ and Rᶜ group, if there is one, is hydrogen. Suitable esters of this type include t-butyloxycarbonyl, diphenylmethoxycarbonyl, triphenylmethoxycarbonyl, and allyloxycarbonyl.

Silyl esters. This category of blocking groups, may conveniently be prepared from a halosilane of the formula: R₃⁴°SiX° wherein X° is a halogen such as chloro or bromo and R⁴' is independently chosen from: alkyl, having 1–6 carbon atoms, phenyl, or phenylalkyl. Suitable esters of this type include t-butyldiphenylsilylcarbonyl.

Pharmaceutically acceptable carboxyl derivatives of the present invention are those derived by reacting I with alcohols, acylating reagents and the like. For example, esters and amides of interest are the above-listed starting materials and final products having the —COX'R$^4$ group at the 3-position; wherein X' is oxygen, sulfur or NR' (R' is H or R$^4$), and R$^4$ is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkyl portion has 1–6 carbon atoms, such as pivaloyloxymethyl; haloalkyl wherein halo is chloro, and the alkyl portion is straight or branched having 1–6 carbon atoms, e.g., 2,2,2-trichloroethyl; alkenyl having 1–4 carbon atoms, such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8–10 carbon atoms, such as benzyloxymethyl, and (4-nitro) benzyloxymethyl.

In addition to the esters (and thio esters) listed above, amides are also embraced by the present invention, i.e., wherein X' is the —NR'— group. Representative of such amides are those wherein R' is selected from the group consisting of hydrogen and alkyl such as methyl and ethyl.

The most preferred —COX'R$^4$ radicals of the present invention are those wherein (relative to Structure I above), X' is oxygen and R$^4$ is hydrogen; loweralkyl having 1–4 carbon atoms; lower alkenyl such as 3-methylbutenyl, allyl, 2,2,2-trichloroethyl, 4-butenyl and the like; benzyl and substituted benzyl such as o-nitrobenzyl, p-nitrobenzyl, pivaloyloxymethyl, 3-phthalidyl; phenacyl, acetonyl; and triorganosilyl, such as trimethylsilyl.

Removal of the preferred protecting groups is categorized as follows: (a) for hydroxyl and amino functionalities bearing p-nitrobenzyloxycarbonyl protection or a carboxyl functionality possessing a p-nitrobenzyl moiety deprotection is accomplished by catalytic hydrogenation over a transition metal catalyst such as palladium supported on carbon, palladium hydroxide on carbon, or plantinum oxide, in an inert solvent or solvent mixtures, which maybe buffered in the usual way, such as tetrahydrofuran, dioxane, ethyl acetate, ethanol, and water, at a temperature of from 0° C. to ambient temperature, at a pressure of from 1 atmosphere to 5 atomspheres of hydrogen, for a period of from a few minutes to twelve hours; (b) for hydroxyl functions covered by a tbutyldimethylsilyl (TBDMS) group removal is accomplished according to the procedure of G. Just and T. J. Liak, *Can. J. Chem.*, 56, 211 (1978), which comprises treating the TBDMS ether derivative with N-tetrabutyl ammonium fluoride in the presence of acetic acid in an inert solvent such as tetrahydrofuran at a temperature of from −78° C. to ambient temperature for from a few minutes to 72 hours; (c) for carboxyl moieties possessing an allyl moeity and for hydroxyl and amino groups bearing an allyloxycarbonyl function deprotection is accomplished by treatment with a combination of triphenyl phosphine, tetrakistriphenylphosphine palladium (O), and 2-ethylhexanoic acid or its sodium or potassium salts in a suitable aprotic solvent such as ethylacetate, methylene chloride, tetrahydrofuran, or diethylether. Use of either sodium or potassium 2-ethylhexanoate provides the corresponding salt; whereas 2-ethylhexanoic acid provides the free carboxylic acid. The process for removing an allylic group from allylic esters, carbonates and carbamates is described in European Patent Application 13,633 (Schering Corp.) and in S. W. McCombie, et al., *Tetrahedron Letters*, 22, 3489 (1981).

PREFERRED VALUES FOR R$^6$ and R$^7$

In the generic structure (I):

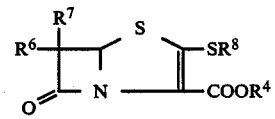

The preferred value for R$^6$ and R$^7$ independently are selected from:

H

CH$_3$CH$_2$

CH$_3$

CH$_3$CH$_2$CH(OH)

FCH$_2$CH(OH)

CF$_3$CH(OH)

CH$_2$OH (CH$_3$)$_2$C(OH)

CH$_3$CF$_2$ $\phi$CH$_2$[$\phi$=phenyl]

(CH$_3$)$_2$CHCH(OH)

CH$_3$CH(NH$_2$)

CH$_3$CH(OH)

HOCH$_2$CH$_2$

CH$_3$O

CH$_3$CH[NH(CH$_3$)]

(CH$_3$)$_2$CH

CH$_3$CH$_2$CH$_2$CH(OH)

HOCH$_2$CH(OH)

CH$_3$O$_2$C

NH$_2$OC

CH$_3$NH(CO)

CH$_2$=CHCH(OH)

HO$_2$CCH$_2$

CF$_3$

CH$_2$=CH

HC≡C

H₂NCH₂

HCF₂CH₂

CH₂=

(HOCH₂)(CH₃)C=

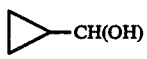

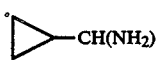

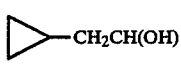

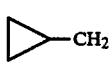

CH₃O₂CCH₂

CH₃OCH₂CH(OH)

ClCH₂CH(OH)

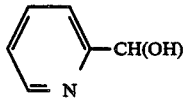

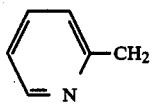

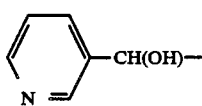

An especially preferred substitution at position 6 finds R⁶=H, and R⁷ selected from: hydrogen, FCH₂CH(OH)—, CH₃CH₂CH(OH)—, CH₃CH₂—, OCH₃, (CH₃)₂CH—,

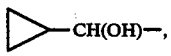

(CH₃)₂C(OH)—, and HOCH₂; when R⁶ is not hydrogen, R⁷ is as designated in this sentence and additionally includes CH₃CH(OH)—.

Relative to the generic description of the compounds of the present invention, I:

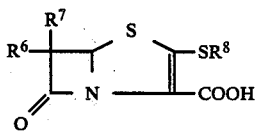

the following representative drawings depict the most preferred configurations:

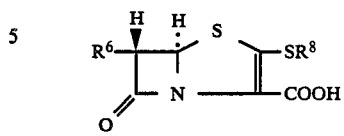

R⁶=CH₃CH₂, (CH₃)₂CH, CH₃O, HOCH₂, for example.

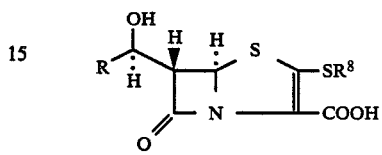

R=FCH₂, CH₃CH₂, for example.

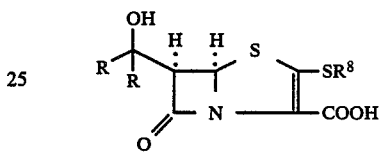

R=CH₃, —CH₂—, for example.

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa, Pseudomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose, Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semisolid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

In the foregoing word description, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents.

The following examples recite a precise scheme of synthesis. It is to be understood that the purpose of this reaction is to further illustrate the invention and not to impose any limitation. Temperature is in °C.

EXAMPLE 1

Preparation of

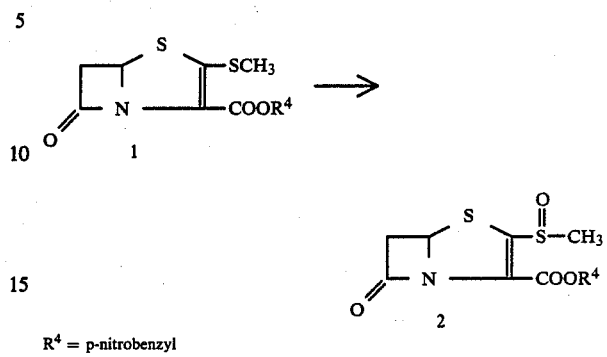

$R^4$ = p-nitrobenzyl

To a stirred solution of 11.3 mg. (0.032 mmol) of penem 1 in 1 ml. of methylene chloride at 0° C. in an ice-H₂O bath is added 7.2 mg. (0.035 mmol) of 85% m-chloroperbenzoic acid. The mixture is stirred at 0° C. under an atmosphere of nitrogen for 1.0 hour after which time an excess of basic resin (Amberlyst-21) is added and stirring continued for 5 minutes. The resin is removed by filtration and the filtrate is purified directly by plate layer chromatography (PLC) using CH₂Cl₂-EtOAc (1:1) as the eluant, to provide 6.5 mg. (55%) of sulfoxides 2 as a white foam; IR(CH₂Cl₂) 1790, 1720, 1690 cm⁻¹; 300 MHZ NMR (CDCl₃)δ: 2.94, 2.98 (s, 3H), 3.74, 3.80 (dd's, J=2, 18, Hz, 1H), 3.94, 4.0 (dd, J=4, 18 Hz, 1H), 5.3 (d's, J=14 Hz, 1H), 5.46 (d's, J=14 Hz, 1H), 5.82, 5.96 (dd's, J=2, 4 Hz, 1H), 7.64 (d's, J=9 Hz, 2H), 8.3 (d, J=9 Hz, 2H).

EXAMPLE 2

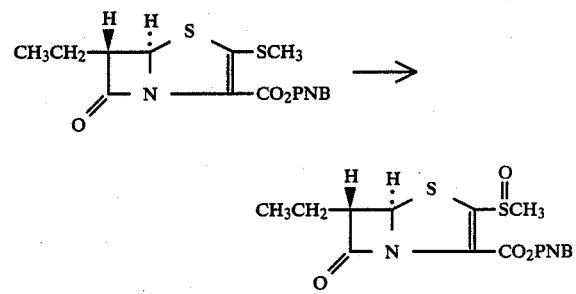

p-Nitrobenzyl (5R,6S)-2-methylsulfinyl-6-ethyl-pen-2-em-3-carboxylate

A solution of 85% m-chloroperoxy benzoic acid (53 mg, 0.26 mmol) in CH₂Cl₂ (1 ml) is added dropwise over a few minutes to an ice-cold, stirring solution of p-nitrobenzyl (5R,6S)-2-methylthio-6-ethyl-pen-2-em-3-carboxylate (94 mg, 0.25 mmol) in anhydrous THF (2 ml). The resulting solution is stirred an additional 30 minutes at 0°, then diluted with EtOAc and washed with H₂O, 5% aqueous NaHCO₃, H₂O, and brine. The organic phase is dried with MgSO₄, filtered, and evaporated in vacuo to provide the title compound as a mixture of sulfoxide isomers.

EXAMPLE 3

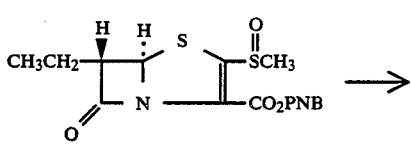

→

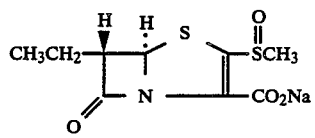

Sodium (5R, 6S)-2-methylsulfinyl-6-ethyl-pen-2-em-3-carboxylate

A solution of p-nitrobenzyl (5R,6S)-2-methylsulfinyl-6-ethyl-pen-2-em-3-carboxylate (50 mg) in THF (9 ml) is diluted with EtOH (4.5 ml) and H₂O (7.0 ml) containing NaHCO₃ (10.6 mg). The resulting solution is added to a prereduced mixture of 10% Pd/C (100 mg) in EtOH (4.5 ml) and the resulting mixture is rapidly stirred under a H₂ atmosphere for 2 hours. The mixture is filtered to remove the catalyst which is washed with H₂O (2×25 ml). The combined filtrate is extracted with Et₂O (2×50 ml) concentrated under vacuum to ca. 10 ml volume, and lyophilized to yield the title compound.

EXAMPLE 4

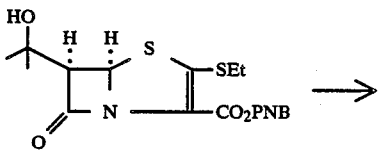

→

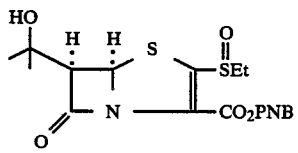

p-Nitrobenzyl (5R,6R)-2-ethylsulfinyl-6-(2-hydroxy-2-propyl)-pen-2-em-3-carboxylate A solution of 85% m-chloroperoxybenzoic acid (112 mg, 0.55 mmol) in CH₂Cl₂ (2.5 ml) is added dropwise over 5 mins. to an ice-cold, stirring solution of p-nitrobenzyl (5R,6R)-2-ethylthio-6-(2-hydroxy-2-propyl)-pen-2-em-3-carboxylate (212 mg, 0.5 mmol) in CH₂Cl₂ (5 ml). The mixture is stirred for 1 hour at 0°, then treated with excess Amberlyst-21 resin and stirred 5 minutes longer. The mixture is filtered and the filtrate is evaporated under vacuum to provide the crude product.

EXAMPLE 5

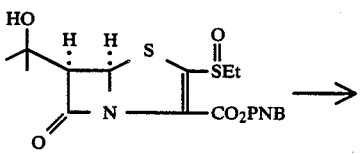

→

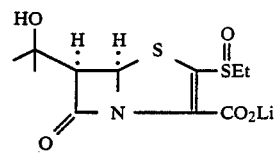

Lithium (5R,6R)-2-ethylsulfinyl-6-(2-hydroxy-2-propyl)-pen-2-em-3-carboxylate A solution of p-nitrobenzyl (5R,6R)-2-ethylsulfinyl-6-(2-hydroxy-2-propyl)-pen-2-em-3-carboxylate (215 mg) in EtOAc (25 ml) is diluted with 1M aqueous NaHCO₃ solution (25 ml) and treated with 10% Pd/C (400 mg). The resulting mixture is stirred under an atmosphere of H₂ for 1 hour and then filtered to remove the catalyst which is washed with more EtOAc and 1M NaHCO₃. The aqueous portion is separated, acidified with 5% aqueous citric acid, and thoroughly extracted with CH₂Cl₂. The organic extracts are briefly dried over Na₂SO₄ and concentrated under vacuum. The residue of (5R,6R)-2-ethylsulfinyl-6-(2-hydroxy-2-propyl)-pen-2-em-3-carboxylic acid is taken up in EtOAc (20 ml) and thoroughly extracted with 0.02M LiOH solution (25 ml). The aqueous phase is separated, and lyophilized to yield the title compound.

EXAMPLE 6

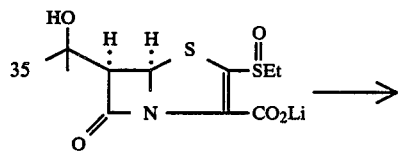

→

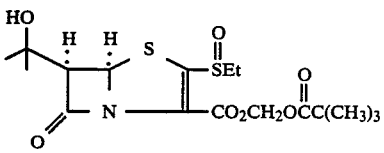

Pivaloyloxymethyl (5R,6R)-2-ethylsulfinyl-6-(-2-hydroxy-2-propyl)-pen-2-em-3-carboxylate Pivaloyloxymethyl bromide (29.3 mg, 0.15 mmol) is added to a suspension of lithium (5R,6R)-2-ethylsulfinyl-6-(2-hydroxy-2-propyl)-pen-2-em-3-carboxylate (29.5 mg, 0.1 mmol) in anhydrous DMF (0.5 ml). The resulting mixture is stirred under a N₂ atmosphere at room temperature for 4 hours. The mixture is diluted with EtOAc, washed repeatedly with water, dried with MgSO₄, filtered, and evaporated under vacuum to afford a residue of the title compound. This material is purified by preparative TLC.

EXAMPLE 7

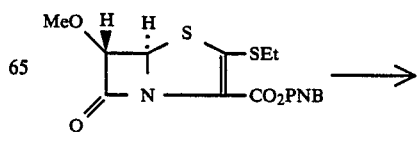

→

-continued

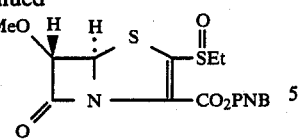

p-Nitrobenzyl (5R,6S)-2-ethylsulfinyl-6-methoxy-pen-2-em-3-carboxylate

A solution of p-nitrobenzyl (5R,6S)-2-ethylthio-6-methoxy-pen-2-em-3-carboxylate (96 mg, 0.24 mmol) in anhydrous DMF (1.2 ml) is diluted with $CH_2Cl_2$ (2.4 ml) and cooled in an ice-bath. A solution of 85% m-chloroperoxybenzoic acid (51 mg, 0.25 mmol) in $CH_2Cl_2$ (1.2 ml) is added dropwise over 2 minutes to the cold, stirring solution. The resulting mixture is kept at 0° for 60 minutes, and then treated with excess Amberlyst-21 resin and stirred and additional 5 minutes. The mixture is filtered and the filtrate is diluted with $CH_2Cl_2$ and washed with 5 portions of $H_2O$. The organic phase is dried over $MgSO_4$, filtered, and evaporated under vacuum to give a crude residue of the title compound which is purified by rapid chromatography on silica gel.

EXAMPLE 8

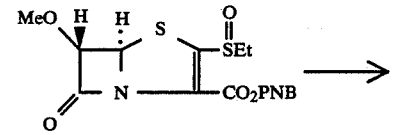

↓

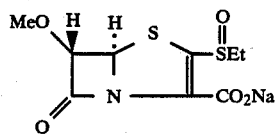

Sodium (5R,6S)-2-ethylsulfinyl-6-methoxy-pen-2-em-3-carboxylate

A mixture of p-nitrobenzyl (5R,6S)-2-ethylsulfinyl-6-methoxy-pen-2-em-3-carboxylate (48 mg, 0.12 mmol) and 10% pd/C (100 mg) in dioxane (8 ml) and $H_2O$ (4 ml) is shaken under a $H_2$ pressure of 45 psi for 60 minutes. The reaction mixture is diluted with $H_2O$ (20 ml) containing $NaHCO_3$ (10 mg, 0.12 mmol) and filtered to remove the catalyst. The filtrate is washed with $Et_2O$ (3×20 ml), concentrated under vacuum to ca. 5 ml volume, and lyophilized to provide the crude product.

EXAMPLE 9

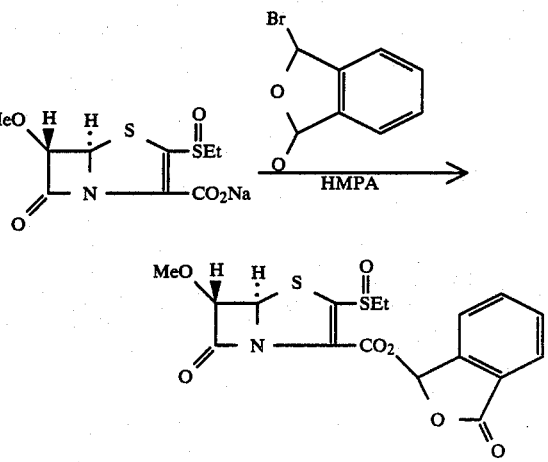

Phthalidyl (5R,6S)-2-ethylsulfinyl-6-methoxy-pen-2-em-3-carboxylate

A mixture of sodium (5R,6S)-2-ethylsulfinyl-6-methoxy-pen-em-3-carboxylate (28 mg, 0.1 mmol) and phthalidyl bromide (32 mg, 0.15 mmol) in anhydrous hexamethylphosphoramide (0.5 ml) is stirred at room temperature and under a $N_2$ atmosphere for 2 hours. The mixture is diluted with $Et_2O$, washed with several portions of $H_2O$, dried with $MgSO_4$, filtered, and evaporated under vacuum. The residue is purified by preparative silica gel chromatography to provide the title compound.

EXAMPLE 10

Preparation of:

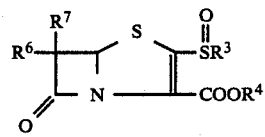

Following the procedures described in the foregoing Examples and text, the compounds listed below are obtained by analogy. PNB=p-nitrobenzyl.

| Compound | $R^6$ | $R^7$ | $R^3$ | $R^4$ | Remarks |
|---|---|---|---|---|---|
| 1 | H | $CH_3CH_2$ | $CH_3$ | $CH_2OCCH_3$ with $\|O$ | Obtained by alkylating $R^4$ = Na compound |
| 2 | H | $CH_3CH_2$ | $CH_3$ | $CH_2OCC(CH_3)_3$ with $\|O$ | Obtained by alkylating $R^4$ = Na compound |
| 3 | H | $CH_3CH_2$ | $CH_3$ | phthalidyl | Obtained by alkylating $R^4$ = Na compound |

-continued

| Compound | $R^6$ | $R^7$ | $R^3$ | $R^4$ | Remarks |
|---|---|---|---|---|---|
| 4 | H | $CH_3CH_2$ | $CH_3$ | $CH_2N$-phthalimido | Obtained by alkylating $R^4$ = Na compound |
| 5 | H | $CH_3CH_2$ | $CH_3$ | $CH_2CH=C(CH_3)_2$ | Obtained by alkylating $R^4$ = Na compound |
| 6 | H | $CH_3CH_2$ | $CH_3$ | $CH_2$-C$_6$H$_4$-$C(CH_3)_3$ | Obtained by alkylating $R^4$ = Na compound |
| 7 | H | $CH_3CH_2$ | $CH_3$ | $CH_2$-C$_6$H$_4$-$OC_6H_5$ | Obtained by alkylating $R^4$ = Na compound |
| 8 | H | $CH_3CH_2$ | $CH_3$ | $CH(CH_3)OCO_2C_2H_5$ | Obtained by alkylating $R^4$ = Na compound |
| 9 | H | $CH_3CH_2$ | $CH_3CH_2$ | PNB, H, Na | |
| 10 | H | $CH_3CH_2$ | $CH_2C_6H_5$ | PNB, H, Na | |
| 11 | H | $HOCH_2$ | $CH_3$ | PNB, H, Na | Hydroxyl group protected by PNBO$_2$C derivative. Cleavage occurs in ester deblocking stage. |
| 12 | H | $HOCH_2$ | $CH_2CH_3$ | PNB, H, Na | Hydroxyl group protected by PNBO$_2$C derivative. Cleavage occurs in ester deblocking stage. |
| 13 | H | $HOCH_2$ | $CH_2CH_3$ | $CH(CH_3)OCO_2C_2H_5$ | Obtained by alkylating $R^4$ = Na. |
| 14 | H | $HOCH_2$ | $CH_2CH_3$ | $CH_2OCOC(CH_3)_3$ | Obtained by alkylating $R^4$ = Na. |
| 15 | H | $HOCH_2$ | $CH_2CH_3$ | phthalidyl | Obtained by alkylating $R^4$ = Na. |
| 16 | H | $(CH_3)_2C(OH)$ | $CH_2CH_3$ | PNB, H, Na | |
| 17 | H | $(CH_3)_2C(OH)$ | $CH_2CH_3$ | $CH_2OCOC(CH_3)_2$ | |
| 18 | H | $(CH_3)_2C(OH)$ | $CH_2CH_3$ | phthalidyl | |
| 19 | $OCH_3$ | $CH_3CH(OH)$ | $CH_2CH_3$ | PNB, H, Na | Hydroxyl group protected as the PNBO$_2$C derivative. Deblocking occurs at ester removal stage. |
| 20 | $CF_3$ | $CH_3CH(OH)$ | $CH_2CH_3$ | PNB, H, Na | |
| 21 | H | $CH_3O$ | $CH_2CH_3$ | PNB, H, Na | |
| 22 | H | $CH_3O$ | $CH_2CH_3$ | $CH_2CH=C(CH_3)_2$ | Via alkylation of $R_4$ = Na intermediate |
| 23 | H | $CH_3O$ | $CH_2CH_3$ | $CH_2OCOC(CH_3)_3$ | Via alkylation of $R_4$ = Na intermediate |
| 24 | H | $CH_3O$ | $CH_2CH_3$ | phthalidyl | Via alkylation of $R_4$ = Na intermediate |
| 25 | H | $CH_3O$ | $CH_2CH_3$ | $CH(CH_3)OCO_2CH_2CH_3$ | Via alkylation of $R_4$ = Na intermediate |
| 26 | H | $CH_3O$ | $CH_3$ | PNB, H, Na | |
| 27 | H | $FCH_2CH(OH)$ | $CH_2CH_3$ | PNB, H, Na | Hydroxyl group protected as PNBO$_2$C derivative. Simultaneously cleaved in ester deblocking stage. |

-continued

| Compound | R⁶ | R⁷ | R³ | R⁴ | Remarks |
|---|---|---|---|---|---|
| 28 | H | CH₃CH(NH₂)- | CH₂CH₃ | PNB, H | Amino group protected as PNBO₂C derivative. Cleaved in ester deblocking reaction. |
| 29 | H | CF₃CH₂ | CH₃ | PNB, H, Na | |
| 30 | H | CH₃O₂CCH₂ | CH₃ | PNB, H, Na | |
| 31 | H | CH₃O₂CCH₂ | CH₃ | phthalidyl | |
| 32 | H | CH₃O₂CCH₂ | CH₃ | CH₂OCOC(CH₃)₂ | |
| 33 | H |  (2-pyridyl)-CH(OH)- | CH₃ | PNB, H | Hydroxyl group protected as PNBO₂C derivative. Deprotected at ester deblocking stage. |
| 34 | H | 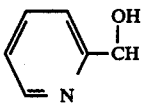 (2-pyridyl)-CH₂- | CH₃ | PNB, H | |
| 35 | H | CH₃CH₂CH(OH)- | CH₃ | PNB, H, Na | Hydroxyl group protected as PNBO₂C derivative. Deprotection occurs in ester deblocking reaction. |
| 36 | H | CF₃CH(OH)- | CH₃CH₂ | PNB, H, Na | Hydroxyl group protected as PNBO₂C derivative. Deprotection occurs in ester deblocking reaction. |
| 37 | H | 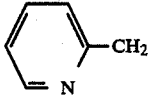 cyclopropyl-CH(OH)- | CH₃CH₂ | PNB, H, Na | Hydroxyl group protected as PNBO₂C derivative. Deprotection occurs in ester deblocking reaction. |
| 38 | H | CF₃ | CH₂C₆H₅ | PNB, H, Na | |
| 39 | H | HOCH₂CH₂ | CH₃ | PNB. H, Na | Hydroxyl group is protected as PNBO₂C derivative which is cleaved in ester deblocking reaction. |
| 40 | H | C₆H₅CH₂ | CH₃CH₂ | PNB, H, K | KHCO₃ replaces NaHCO₃ in ester reduction reaction. |
| 41 | H | (CH₃)₂CH | CH₃CH₂ | PNB, H, Na | |
| 42 | H | CH₃O | CH₃CH₂ | CH₂CH=CH₂, K | |
| 43 | H | HOCH₂ | CH₃CH₂ | CH₂CH=CH₂, K | The hydroxyl group is protected as its t-butyl-dimethylsilyl ether which is deprotected using Bu₄NF/HOAc either prior to or after sulfur oxidation and before ester deprotection. |
| 44 | H | FCH₂CH(HO)- | CH₃CH₂ | CH₂CH=CH₂, K | The hydroxyl group is protected as its t-butyl-dimethylsilyl ether which is deprotected using Bu₄NF/HOAc either prior to or after sulfur oxidation and before ester deprotection. |
| 45 | H | (CH₃)₂C(OH)- | CH₃CH₂ | CH₂CH=CH₂, K | The hydroxyl group is protected as its t-butyl-dimethylsilyl ether which is deprotected using Bu₄NF/HOAc either prior to or after sulfur oxidation and before ester deprotection. |

-continued

| Compound | R⁶ | R⁷ | R³ | R⁴ | Remarks |
|---|---|---|---|---|---|
| 46 | H | HO–CH(CH₂CH₃) | CH₃ | CH₂CH=CH₂, K | The hydroxyl group is protected as its t-butyl-dimethylsilyl ether which is deprotected using Bu₄NF/HOAc either prior to or after sulfur oxidation and before ester deprotection. |

EXAMPLE 11

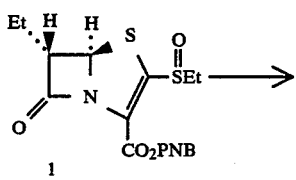
1

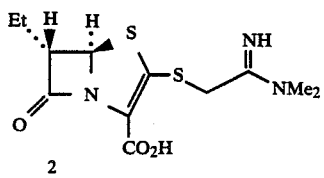
2

Preparation of
±-(5R,6S)-6-Ethyl-2-[N,N-dimethylcarbamimidoylmethylthio]-pen-2-em-3-carboxylate To a stirred solution of 82.0 mg (0.2 mmol) of penem sulfoxide 1 in 1.5 ml of DMF at −20° C. under an atmosphere of nitrogen is added a solution of 30.8 mg (0.2 mmol) of N,N-dimethyl-2-mercaptoacetamidium hydrochloride in 0.5 ml DMF and 25.8 mg (0.2 mmol) of diisopropylethylamine. The mixture is stirred at −20° C. under N₂ for 5 minutes and the resulting transformed penem precipitated by the addition of Et₂O. After decantation of the supernatant, the separated product is washed analogously with Et₂O and dried briefly in vacuo. The residue is then dissolved in 4 ml of THF, 2 ml H₂O, and 0.5 ml of 0.1M pH 7.1 phosphate buffer, and hydrogenated with 40 mg of PtO₂ catalyst at 50 psi at ambient temperature for 3.5 hours. The catalyst is removed by filtration through filter aid, washed well with EtOAc and H₂O. The filtrate is further diluted with EtOAc and H₂O and the aqueous is separated, washed further with EtOAc, and concentrated in vacuo. The concentrate is purified by reverse phase chromatography to give the final product 2.

EXAMPLE 12

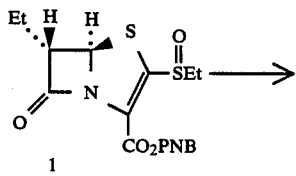
1

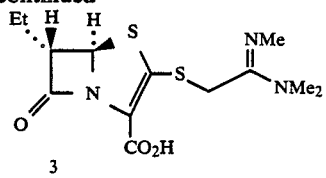
3

Preparation of
(±)-(5R,6S)-6-Ethyl-2-[N,N,N'-trimethylcarbamimidoylmethylthio]-pen-2-em-3-carboxylate To a stirred solution of 100 mg (0.24 mmols) of penem sulfoxide 1 in 1.8 ml of DMF at −20° C. under an atmosphere of nitrogen is added a solution of 52.8 mg (0.24 mmols) of N,N,N'-trimethyl-2-mercaptoacetamidinium tetrafluoroborate in 0.6 ml DMF and 31.0 mg (0.24 mmols) of diisopropylethylamine. The mixture is stirred at −20° C. under nitrogen for 5 minutes and diethylether is then added to effect the separation of the adduct. After washing and drying in vacuo, the adduct is dissolved in 4 ml THF, 2 ml H₂O, and 0.5 ml of 0.1M pH 7.1 phosphate buffer and is hydrogenated with 50 mg of PtO₂ catalyst at 50 psi on a Parr apparatus for 3.0 hours. The final product 3 is isolated by conventional techniques.

EXAMPLE 13

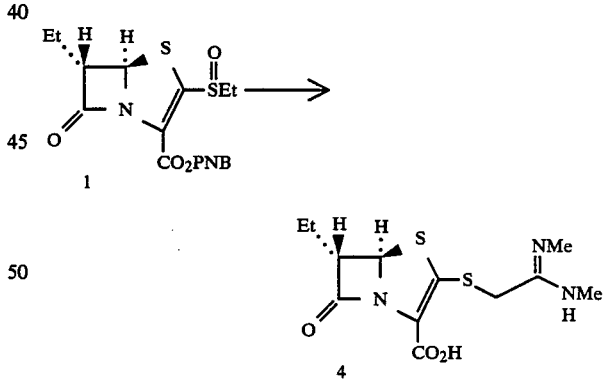

Preparation of
(±)-(5R,6S)-6-Ethyl-2-[N,N'-dimethylcarbamimidoylmethylthio]-pen-2-em-3-carboxylate To a stirred solution of 123.0 mg (0.3 mmol) of penem sulfoxide 1 in 2 ml of DMF at −20° C. under an atmosphere of nitrogen is added a solution of 61.8 mg (0.3 mmol) of N,N'-dimethyl-2-mercaptoacetamidinium tetrafluoroborate in 0.75 ml DMF and 38.8 mg (0.3 mmol) of diisopropylethylamine. The mixture is stirred at −20° C. for 5 minutes and diethyl ether is then added to separate the transformed penem. The supernatant is removed by decantation and the separated material washed with Et₂O (2X) and dried in vacuo for a short time. The material is then dissolved in 4 ml THF, 2 ml H₂O, and 0.5 ml of 0.1M pH 7.1 phosphate buffer. The solution is shaken with 25 mg of PtO₂ catalyst on a Parr apparatus under 50 psig of hydrogen for 4.0 hours. After this time the final product 4 is isolated by conventional procedures.

EXAMPLE 14

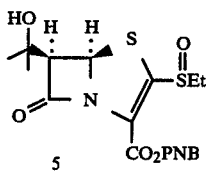

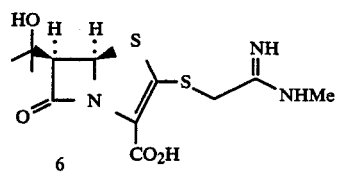

Preparation of (±)-(5R,6R)-6-[1′-hydroxyisopropyl]-2-[N-methylcarbamimidoylmethylthio]-pen-2-em-3-carboxylate To a stirred solution of 88.0 mg (0.2 mmol) of penem sulfoxide 5 in 2.0 ml of DMF at −35° C. under an atmosphere of nitrogen is added a solution of 28.0 mg (0.2 mmol) of N-methyl-2-mercaptoacetamidinium hydrochloride in 0.5 ml DMF and 25.8 mg (0.2 mmol) of diisopropylethylamine. The mixture is stirred at −35° C. for 5 minutes and diethylether is then added. The supernatant is decanted away from the separated material which is then washed analogously with Et₂O. The material is dissolved in 4 ml THF, 2 ml H₂O, and 0.5 ml of pH 7.1 phosphate buffer and 30 mg of PtO₂ catalyst is added. The mixture is hydrogenated on a Parr apparatus at 50 psi and ambient temperature for 2.5 hours. After this time the product 6 is isolated by conventional procedures.

EXAMPLE 15

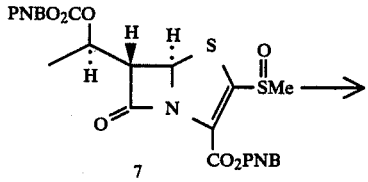

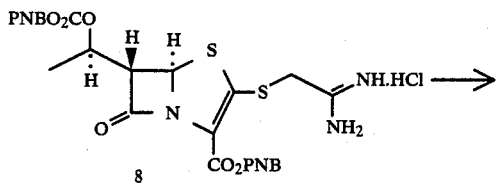

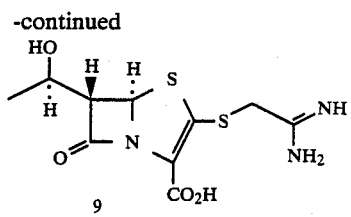

(5R,6S)-2-Carbamimidoylmethylthio-6-[(R)-1-hydroxypropyl]-pen-2-em-3-carboxylic acid (9)

Bis protected sulfoxide 7 (60.6 mg, 0.1 mmol) in anhydrous DMF (0.8 ml) is stirred in a dry ice-CCl₄ bath (−23°) and under a N₂ atmosphere. A solution of carbmimidoylmethyl mercaptan hydrochloride (12.7 mg, 0.1 mmol) in DMSO (0.2 ml) and iPr₂NEt (19.2 ml, 0.11 mmol) are added dropwise and simultaneously. The resulting mixture is stirred for 10 minutes at −20°, then added to Et₂O (16 ml) and shaken. The Et₂O phase is decanted from the oily residue of crude displacement product 8 which is washed with more Et₂O (2×6 ml). The oily residue is taken up in THF (4 ml) and 0.1M pH 7 phosphate buffer (3 ml) and hydrogenated at atmospheric pressure with 10% PdlC (30 mg). After 1 hour, more catalyst (30 mg) is added and the hydrogenation is continued for an additional 1 hour. The mixture is filtered and the catalyst is washed with H₂O (2×5 ml). The filtrate is washed with EtOAc (2×10 ml), concentrated under vacuum to ca. 2 ml, and streaked on two 0.25 mm×20×20 cm. Analtech RPS-f plates which are developed with 10% EtOH/H₂O in a cold room. The major UV visible zone is removed and eluted with 4:1 MeCN-H₂O (4×10 ml). The eluant is washed with hexanes, (2×20 ml) concentrated under vacuum, and lyophilized to provide the title compound 9.

EXAMPLE 16

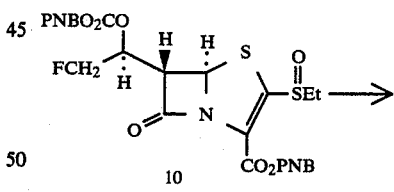

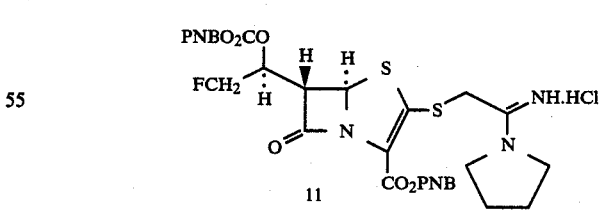

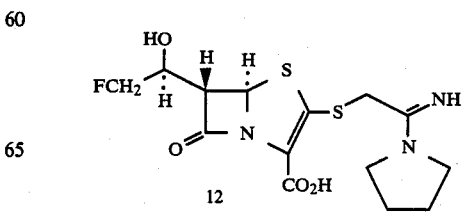

(5R,6S)-2-(N,N-tetramethylene)carbamimidoylmethylthio-6-[(S)-1-hydroxy-2-fluoroethyl]-pen-2-em-3-carboxylic acid (12)

A solution of sulfoxide 10 (56 mg, 0.09 mmol) in DMF (0.6 ml) is cooled in a dry ice —CCl$_4$ bath and stirred under a N$_2$ atmosphere. A solution of (N,N-tetramethylene)carbamimidoylmethyl mercaptan hydrochloride (16.3 mg, 0.09 mmol) in DMSO (0.15 ml) is added followed by iPr$_2$NEt (15.7 ml, 0.09 mmol) and the resulting solution is stirred at ca. −20° for 15 minutes. The solution is added to Et$_2$O (10 ml) and centrifuged to give an oily precipitate of crude 11. The precipitate is washed with Et$_2$O (2×5 ml), taken up in THF (3.6 ml) and 0.1M pH 7.1 potassium phosphate buffer (2.7 ml) and hydrogenated with 10% Pd/C (50 mg) at 45 psi for 2 hours. The mixture is filtered and the catalyst is washed with H$_2$O (2×5 ml). The aqueous filtrate is washed with EtOAc (3×10 ml), concentrated under vacuum to ca. 2 ml, and changed onto a Dowex 50×2 column (40 ml,K form). The column is eluted with H$_2$O in a cold room. The product fractions are located by UV, combined, concentrated, and lyophilized to yield the title compound 12.

EXAMPLE 17

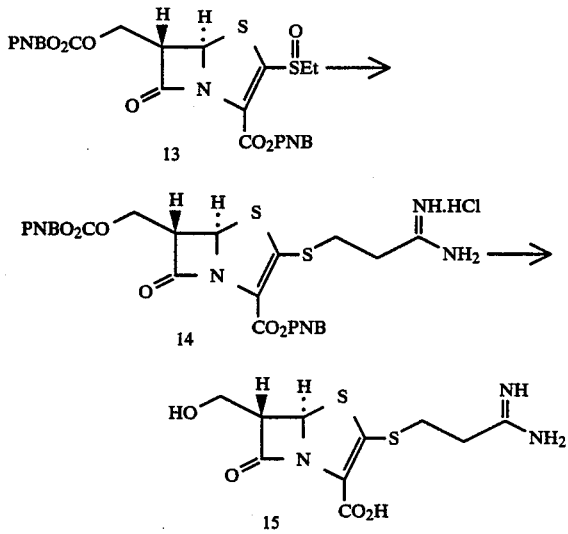

(5R,6S)-2-Carbamimidoylethylthio-6-hydroxymethyl-pen-2-em-3-carboxylic acid (15)

Sulfoxide 13 (27.2 mg, 0.046 mmol) is dissolved in anhydrous DMF (0.35 ml) under a N$_2$ atm. and the solution is cooled in a dry ice —CCl$_4$ bath. Carbamimidoylethylmercaptan hydrochloride (5 mg, 0.046 mmol) in DMSO (0.1 ml) and iPr$_2$NEt (8.7 ml, 0.05 mmol) are added and the resulting solution is stirred for 15 minutes at −20°. The solution is added to Et$_2$O (8 ml) and shaken. The ET$_2$O phase is decanted from the oily residue which is washed with more ET$_2$O (2×3 ml). The oily residue of crude 14 is taken up in THF (1.8 ml) and 0.1M pH 7 potassium phosphate buffer (1.4 ml) and hydrogenated at 45 psi with 10% Pd/C (50 mg) for 2 hours. The mixture is filtered and the catalyst is washed with H$_2$O (2×3 ml). The aqueous filtrate is washed with EtOAc (2×5 ml), concentrated in vacuo to ca. 1 ml, and streaked on a 0.25 mm×20×20 cm Analtech RPS-F plate which is developed with 10% EtOH/H$_2$O. The desired UV visible band is removed and extracted with 4:1 MeCN-H$_2$O (4×5 ml). The extracts are washed with hexanes (2×10 ml), concentrated in vacuo, and lyophilized to afford the title compound 15.

EXAMPLE 18

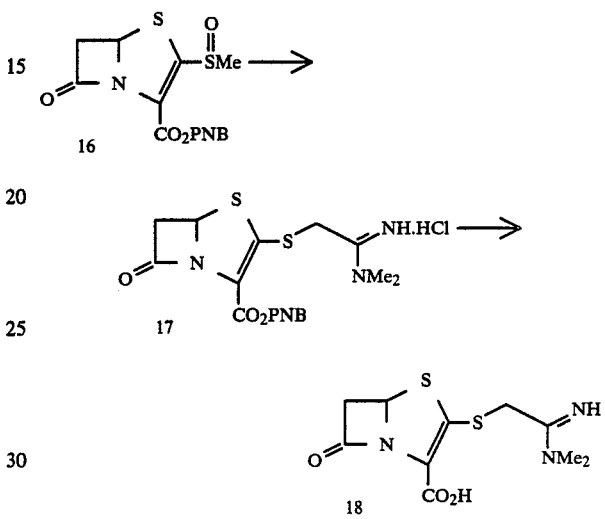

2-(N,N-Dimethyl)carbamimidoylmethylthio-pen-2-em-3-carboxylic acid (18)

A solution of sulfoxide 16 (1.47 g, 4 mmol) in anhydrous DMF (12 ml) is cooled in a dry ice —CCl$_4$ bath under a N$_2$ atm. and treated simultaneously and dropwise over 4 minutes with iPr$_2$NEt (0.77 ml, 4.4 mmol) and a solution of (N,N-dimethylcarbamimidoylmethyl mercaptan hydrochloride (0.62 g, 4 mmol) in DMSO (8 ml). After stirring for 10 minutes at −20°, the mixture is added to a rapidly stirring mixture of supercel (16 g) in Et$_2$O (400 ml). The mixture is stirred for a few minutes and filtered. The supercel pad is washed with more Et$_2$O (400 ml) and sucked dry under a rubber dam.

The crude intermediate 17 is extracted from the supercel by successive washing with THF (100 ml)-H$_2$O(30 ml), THF (20 ml), and 0.1M pH 7.1 phosphate buffer (110 ml). The combined extracts are divided into two equal portions and each is hydrogenated with 10% Pd/C (0.7 g) for 2 hours at 45 psi. The mixture is filtered and the filtrate is washed with Et$_2$O (2×250 ml). The aqueous portion is concentrated under vacuum and charged onto a Dowex 50W×4 column (500 ml, Na form, 200–400 mesh) which is eluted with H$_2$O in a cold room. The appropriate fractions, as determined by UV spectroscopy, are combined, concentrated under vacuum, and lyophilized to afford the title compound 18.

EXAMPLE 19

Following the procedures of the foregoing text and examples, the following "carbamimidoyl" embodiments of the present invention are obtained.

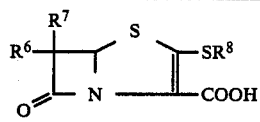

| Compound | R⁶ | R⁷ | R⁸ |
|---|---|---|---|
| 19 | H | CH₃CH₂ | CH₂C(=NH)—NH₂ |
| 20 | H | CH₃CH₂ | CH₂C(=NH)—NHCH₃ |
| 21 | H | CH₃CH₂ | CH₂C(=NH)—NHCH₂CH₃ |
| 22 | H | CH₃CH₂ | CH₂C(=NH)—NHCH(CH₃)₂ |
| 23 | H | CH₃CH₂ | CH₂C(=NH)—NHCH₂C₆H₅ |
| 24 | H | CH₃CH₂ | CH₂C(=NH)—NHCH₂-(2-pyridyl) |
| 25 | H | CH₃CH₂ | CH₂C(=NH)—NHC₆H₅ |
| 26 | H | CH₃CH₂ | CH(CH₃)C(=NH)—NH₂ |
| 27 | H | CH₃CH₂ | CH(CH₃)C(=NH)—NHCH₃ |
| 28 | H | CH₃CH₂ | CH(CH₃)C(=NH)—N(CH₃)₂ |
| 29 | H | CH₃CH₂ | CH(CH₂CH₃)C(=NH)—NH₂ |
| 30 | H | CH₃CH₂ | CH₂CH₂C(=NH)—NH₂ |
| 31 | H | CH₃CH₂ | CH₂CH₂C(=NH)—N(CH₃)₂ |
| 32 | H | CH₃CH₂ | CH₂CH₂CH₂C(=NH)—NH₂ |
| 33 | H | CH₃CH₂ | CH₂C(=NH)—NHCH₂-(4-pyridyl) |
| 34 | H | CH₃CH₂ | CH₂C(=NH)—N(CH₃)CH₂CH₃ |
| 35 | H | CH₃CH₂ | CH₂C(=NH)—N(morpholino) |

-continued

[structure: R6, R7 on β-lactam with S-C(=C-SR8)-COOH side chain]

| Compound | R⁶ | R⁷ | R⁸ |
|---|---|---|---|
| 36 | H | CH₃CH₂ | CH₂C(=NH)—N(CH₂CH₃)₂ |
| 37 | H | CH₃CH₂ | CH₂C(=NH)—N(pyrrolidine) |
| 38 | H | CH₃CH₂ | CH₂C(=NH)—N(azetidine) |
| 39 | H | CH₃CH₂ | CH₂C(=N—CN)—NH₂ |
| 40 | H | CH₃CH₂ | CH₂C(=N—SO₂NH₂)—NH₂ |
| 41 | H | CH₃CH₂ | CH₂—(4,5-dihydroimidazol-2-yl), NH |
| 42 | H | CH₃CH₂ | CH₂—(1-methyl-4,5-dihydroimidazol-2-yl) |
| 43 | H | CH₃CH₂ | CH₂—(1-methylbenzimidazol-2-yl) |
| 44 | H | CH₃CH₂ | CH₂C(=NCH₃)—N(pyrrolidine) |
| 45 | H | CH₃CH₂ | CH₂C(=NCH₂CH₃)—N(CH₃)₂ |
| 46 | H | CH₃CH₂ | CH₂C(=NH)—NHN(CH₃)₂ |
| 47 | H | CH₃CH₂ | CH₂C(=NH)—NHNH—(2-pyridyl) |
| 48 | H | CH₃CH₂ | (5-methyl-3-(methylamino)-3,4-dihydro-2H-pyrrol-2-yl) |

-continued

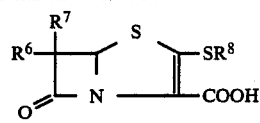

| Compound | R⁶ | R⁷ | R⁸ |
|---|---|---|---|
| 49 | H | CH₃CH₂ | (pyrrolo-imidazoline bicyclic) |
| 50 | H | CH₃CH₂ | CH₂–C(=N)–N(CH₃)– (6-membered ring with N-CH₃) |
| 51 | H | CH₃CH₂ | CH₂–C(=N)–N(CH₂CO₂H)– (5-membered ring) |
| 52 | H | HOCH₂ | CH₂C(=NH)–NH₂ |
| 53 | H | HOCH₂ | CH(CH₃)C(=NH)–NH₂ |
| 54 | H | HOCH₂ | CH₂C(=NH)–NHCH₃ |
| 55 | H | HOCH₂ | CH₂C(=NH)–N(CH₃)₂ |
| 56 | H | HOCH₂ | CH₂C(=NCH₃)–NHCH₃ |
| 57 | H | HOCH₂ | CH₂C(=NCH₃)–N(CH₃)₂ |
| 58 | H | HOCH₂ | CH₂C(=NH)–NHCH₂CH₃ |
| 59 | H | HOCH₂ | CH₂CH₂C(=NH)–N(CH₃)₂ |
| 60 | H | HOCH₂ | CH₂–C(=N)–NH– (5-membered ring, NH) |
| 61 | H | HOCH₂ | CH₂–C(=N)–N(CH₃)– (5-membered ring, N-CH₃) |

-continued $$\begin{array}{c} R^6 \underset{O}{\overset{R^7}{\diagdown}} \underset{N}{\overset{S}{\diagdown}} \underset{COOH}{\overset{SR^8}{\diagup}} \end{array}$$

| Compound | R⁶ | R⁷ | R⁸ |
|---|---|---|---|
| 62 | H | HOCH₂ | CH₂C(=NH)—N(CH₃)CH₂CH₃ |
| 63 | H | HOCH₂ | CH₂C(=NH)—N(morpholino) |
| 64 | H | HOCH₂ | CH₂C(=NH)—N(pyrrolidino) |
| 65 | H | HOCH₂ | (2-methylamino-1-pyrrolinyl) |
| 66 | H | FCH₂CH(OH) | CH₂C(=NH)—NH₂ |
| 67 | H | FCH₂CH(OH) | CH₂C(=NH)—NH₂ |
| 68 | H | FCH₂CH(OH) | CH₂C(=NH)—N(CH₃)₂ |
| 69 | H | FCH₂CH(OH) | CH₂C(=NCH₃)—NHCH₃ |
| 70 | H | FCH₂CH(OH) | CH₂C(=NH)—N(CH₃)₂ |
| 71 | H | FCH₂CH(OH) | CH₂C(=NH)—NHCH₂CH₃ |
| 72 | H | FCH₂CH(OH) | CH₂C(=NH)—N(CH₃)CH₂CH₃ |
| 73 | H | FCH₂CH(OH) | CH₂C(=NH)—N(morpholino) |
| 74 | H | FCH₂CH(OH) | CH(CH₃)C(=NH)—NH(CH₃) |
| 75 | H | FCH₂CH(OH) | CH₂C(=NH)—N(azetidinyl) |
| 76 | H | FCH₂CH(OH) | CH(CH₃)C(=NH)—NH₂ |
| 77 | H | FCH₂CH(OH) | CH₂CH₂C(=NH)—NH₂ |

-continued

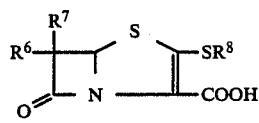

| Compound | R⁶ | R⁷ | R⁸ |
|---|---|---|---|
| 78 | H | FCH₂CH(OH) | CH₂CH₂C(=NH)—N(CH₃)₂ |
| 79 | H | FCH₂CH(OH) | CH₂—C(=N)(NH) cyclic (imidazoline, NH) |
| 80 | H | FCH₂CH(OH) | CH₂—C(=N)(NCH₃) cyclic (imidazoline, N-CH₃) |
| 81 | H | FCH₂CH(OH) | CH₂—C(=N)(NCH₃) cyclic (tetrahydropyrimidine, N-CH₃) |
| 82 | H | FCH₂CH(OH) | cyclic C(=N)(NHCH₃) pyrroline |
| 83 | H | CH₃CH₂CH(OH) | CH₂C(=NH)—NHCH₃ |
| 84 | H | CH₃CH₂CH(OH) | CH₂C(=NH)—N(CH₃)₂ |
| 85 | H | CH₃CH₂CH(OH) | CH₂C(=NCH₃)—NHCH₃ |
| 86 | H | CH₃CH₂CH(OH) | CH₂C(=NCH₃)—N(CH₃)₂ |
| 87 | H | CH₃CH₂CH(OH) | CH₂C(=NH)—NHCH₂CH₃ |
| 88 | H | CH₃CH₂CH(OH) | CH₂C(=NH)—N(pyrrolidinyl) |
| 89 | H | CH₃CH₂CH(OH) | CH₂—C(=N)(NH) cyclic (imidazoline, NH) |
| 90 | H | (CH₃)₂C(OH) | CH₂C(=NH)—NH₂ |

-continued

| Compound | R6 | R7 | R8 |
|---|---|---|---|
| 91 | H | (CH₃)₂C(OH) | CH₂C(=NCH₃)—NHCH₃ |
| 92 | H | (CH₃)₂C(OH) | CH₂C(=NH)—N(CH₃)₂ |
| 93 | H | (CH₃)₂C(OH) | CH₂C(=NCH₃)—N(CH₃)₂ |
| 94 | H | cyclopropyl-CH(OH) | CH₂C(=NH)—NH₂ |
| 95 | H | cyclopropyl-CH(OH) | CH₂C(=NH)—N(CH₃)₂ |
| 96 | H | cyclopropyl-CH(OH) | CH₂C(=NH)—N(pyrrolidinyl) |
| 97 | H | cyclopropyl-CH(OH) | CH₂C(=NCH₃)—N(CH₃)₂ |
| 98 | H | cyclopropyl-CH(OH) | CH₂-(4,5-dihydroimidazol-2-yl) |
| 99 | H | CH₃O | CH₂C(=NH)—N(CH₃)₂ |
| 100 | CH₃CH(OH) | CH₃O | CH₂C(=NH)—NH₂ |
| 101 | CH₃CH(OH) | CH₃O | CH₂C(=NH)—N(CH₃)₂ |
| 102 | CH₃CH(OH) | CH₃O | CH₂C(=NCH₃)—NHCH₃ |
| 103 | CH₃CH(OH) | CH₃O | CH₂C(=NCH₃)—N(CH₃)₂ |
| 104 | CH₃CH(OH) | CH₃O | CH₂C(=NH)—N(pyrrolidinyl) |
| 105 | H | (CH₃)₂CH | CH₂C(=NH)—NH₂ |
| 106 | H | (CH₃)₂CH | CH₂C(=NH)—N(CH₃)₂ |
| 107 | H | HO₂CCH₂ | CH₂C(=NH)—NH₂ |

-continued $$\begin{array}{c} R^7 \\ R^6 \diagup \diagdown \diagup S \diagdown \\ \phantom{R^6}\diagdown \diagup \diagdown SR^8 \\ O \phantom{=} N \phantom{====} COOH \end{array}$$

| Compound | R⁶ | R⁷ | R⁸ |
|---|---|---|---|
| 108 | H | 3-pyridyl-CH(OH)- | CH₂C(=NH)-NH₂ |
| 109 | CF₃ | CH₃CH(OH)- | CH₂-C(=NCH₃)-NHCH₃ |
| 110 | CF₃ | CH₃CH(OH)- | CH₂-C(=NCH₃)-N(CH₃)₂ |
| 111 | CH₃O | CH₃CH(OH)- | CH₂-C(=⁺N(CH₃)₂)-N(CH₃)₂ |
| 112 | CH₃O | CH₃CH(OH)- | CH₂-C(=NH)-NHC₂H₅ |
| 113 | CH₃O | CH₃CH(OH)- | CH₂C(=NH)-N(C₂H₅)₂ |
| 114 | CH₃O | CH₃CH(OH)- | CH₂-C(=NH)-NHCH(CH₃)₂ |
| 115 | CH₃O | CH₃-CH(OH)- | CH₂-C(=NH)-NHC(CH₃)₃ |
| 116 | CH₃O | CH₃-CH(OH)- | CH(CH₃)-C(=NH)-N(CH₃)₂ |
| 117 | CF₃ | CH₃-CH(OH)- | CH(OCH₃)-C(=NH)-NH₂ |
| 118 | CH₃O | CH₃-CH(OH)- | C(=CH₂)-C(=NH)-NH₂ |
| 119 | CH₃O | CH₃-CH(OH)- | CH(CH=CH₂)-C(=NH)-NH₂ |
| 120 | CH₃O | CH₃-CH(OH)- | CH₂CH(OCH₃)-C(=NH)-NH₂ |
| 121 | CH₃ | CH₃-CH(OH)- | CH₂-CH(OH)-C(=NH)-NH₂ |

-continued

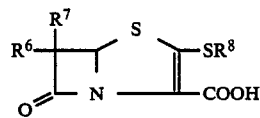

| Compound | R⁶ | R⁷ | R⁸ |
|---|---|---|---|
| 122 | $CH_3$ | $CH_3-CH(OH)-$ | $CH_2-C(=N-OCH_3)-C(=NH)-NH_2$ |
| 123 | $CH_3$ | $CH_3-CH(OH)-$ | $CH_2-CH(N(CH_3)_2)-C(=NH)-NH_2$ |
| 124 | $CH_3$ | $CH_3-CH(OH)-$ | $CH_2-CH(N(CH_3)_3 Cl^-)-C(=NH)-NH_2$ |
| 125 | $CH_3O$ | $CH_3-CH(OH)-$ | $CH_2-CH(SCH_3)-C(=NH)-NH_2$ |
| 126 | $HOCH_2$ | $CH_3-CH(OH)-$ | $CH_2-C(=NH)-NHOCH_3$ |
| 127 | $CH_3O$ | $CH_3-CH(OH)-$ | $CH_2-C(=NH)-N(CH_3)(OCH_3)$ |
| 128 | $CF_3$ | $CH_3-CH(OH)-$ | $CH_2CH_2CH_2-C(=NH)-NH_2$ |
| 129 | $CF_3$ | $CH_3-CH(OH)-$ | $CH_2-C(CH_3)_2-C(=NH)-NH_2$ |
| 130 | $CH_3O$ | $CH_3-CH(OH)-$ | $CH_2CH_2-C(=NH)-N(CH_3)_2$ |
| 131 | $CF_3$ | $CH_3-CH(OH)-$ | $-CH_2-C(=NH)-N\text{(pyrrolidinyl)}$ |
| 132 | $CH_3O$ | $CH_3-CH(OH)-$ | $CH_2-C(=NH)-N\text{(morpholinyl)}$ |
| 133 | $HOCH_2$ | $CH_3-CH(OH)-$ | $CH_2-C(=NH)-N\text{(piperidinyl)}$ |
| 134 | $CF_3$ | $CH_3-CH(OH)-$ | $CH_2-C(=NH)-N\text{(4-methylpiperazinyl)}$ |

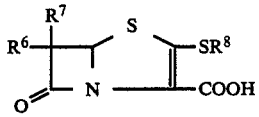

-continued

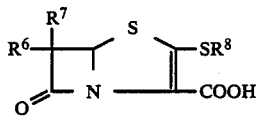

| Compound | R⁶ | R⁷ | R⁸ |
|---|---|---|---|
| 148 | F | CH₃—CH(OH)— | —CH(CH₃)—CH₂—C(=NH)—NH₂ |
| 149 | F | CH₃—CH(OH)— | —CH₂—CH(CH₃)—C(=NH)—NH₂ |

EXAMPLE 20

Preparation of Pharmaceutical Compositions

One such unit dosage form is prepared by mixing 120 mg of the compound of Example 16 (Compound A) with 20 mg of lctose and 5 mg of magnesium stearate and placing the 145 mg mixture into a No. 3 gelatin capsule. Similarly, by employing more of the active ingredient and less lactose, other odsage forms can be put up in No. 3 gelatin capsules, and, should it be necessary to make more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (16 mg) and rough-screened. It is dried at 45° C. and screened again through No. 16 screens. The balance of the cornstarch and magnesium stearate is added and the mixture is compressed into tablets,, approximately 0.5 inch in diameter each weighing 800 mg.

| | PER TABLET |
|---|---|
| PARENTERAL SOLUTION | |
| *Ampoule:* | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water to | 1 ml. |
| OTIC SOLUTION | |
| Compound A | 100 mg. |
| Benzalkonium chloride | 0.1 mg. |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound having the structural formula:

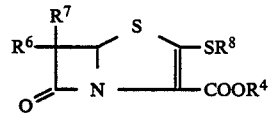

wherein R⁴ is H, a carboxylate salt cation, removable protecting group, or a pharmaceutically acceptable salt, ester or amide moiety; wherein: R⁶ and R⁷, are independently selected from the group consisting of substituted and unsubstituted: hydrogen, alkyl, alkenyl, alkoxyl, and alkynyl having 1-10 carbon atoms; halo; hydroxyl; carboxyl; cyano; cycloalkyl, cycloalkylalkyl, and alkylcycloalkyl having 3-6 carbon atoms in the cycloalkyl ring and 1-6 carbon atoms in the alkyl moiety; aryl, aralkyl, aralkenyl, and aralkynyl wherein the aryl moiety is phenyl and aliphatic portion has 1-6 carbon atoms; heteroaryl, heteroaralkyl, heterocyclyl, and heterocyclylalkyl, wherein the alkyl moiety has 1-6 carbon atoms and the heteroatoms are selected from ON, N and S; R⁶ and R⁷ may be joined to form a cyclicalkyl having, together with the carbon atom to which they are attached, 3-6 carbon atoms; wherein the substituent or substituents on R⁶, and R⁷ are independently selected from chloro, fluoro, hydroxy, bromo, alkoxyl having 1-6 carbon atoms, mercapto, carboxyl, cyano, azido, amino, mono- and dialkylamino (each alkyl having 1-6 carbon atoms), ureido, alkylthio having 1-6 carbon atoms; and R⁸ is a carbamimidoyl selected from the group consisting of:

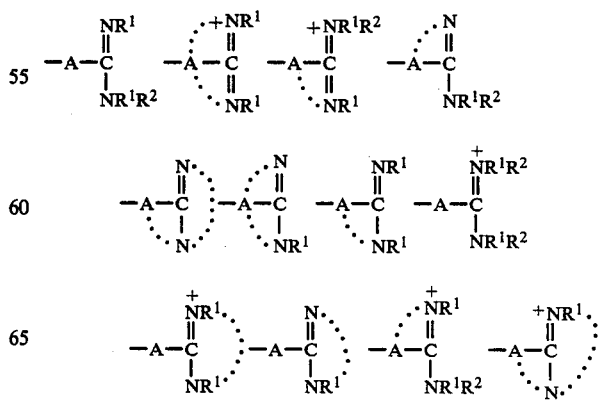

wherein: A is a single, direct bond, or A, the cyclic or acyclic connector, is selected from the group consisting of alkyl, alkenyl, and alkynyl having 1–10 carbon atoms which may be interrupted by a hetero atoms selected from O, S or N, or by a ring such as phenyl, cycloalkyl, cycloalkenyl, heterocyclyl or heteroaryl wherein such cyclic interruptions comprise 3–6 ring atoms selected from C, O, S and N; cycloalkyl, cycloalkenyl having 3–6 carbon atoms; heterocyclyl; heteroaryl; and phenyl; $R^1$ and $R^2$ are independently selected from: hydrogen, $N(R^a)_2$, $OR^a$, ($R^a$ is $C_{1-6}$alkyl), CN, $SO_2NH_2$ and the previously defined, but monovalent, values for the group A; and wherein the dotted lines indicate provision for cyclic structures formed by the joinder of the indicated nitrogen atom and the connector group A and by the joinder of the indicated nitrogen atoms; when $R^6/R^7$ is $CH_3CH(OH)$—, $R^7/R^6$ is not hydrogen.

2. A compound according to claim 1 wherein $R^1$ and $R^2$ are independently selected from: hydrogen, alkyl, aryl, cycloalkyl, alkylaryl, aralkyl, alkylarylalkyl, heterocyclyl, and heteroaryl.

3. A compound according to claim 1 wherein: $R^1$ and $R^2$ are independently selected from the group consisting of hydrogen; substituted and unsubstituted: straight and branched loweralkyl having from 1 to 6 carbon atoms; cycloalkyl having 3 to 6 carbon atoms; cycloalkylalkyl wherein the cycloalkyl moiety comprises 3 to 6 carbon atoms and the alkyl moiety comprises 1 to 6 carbon atoms; alkylcycloalkyl wherein the alkyl moiety comprises 1 to 6 carbon atoms and the cycloalkyl moiety comprises 3 to 6 carbon atoms; phenyl; phenylalkyl having 7–10 carbon atoms; heterocyclyl (saturated and unsaturated) comprising mono- and bicyclic structures having from 5 to 10 ring atoms, wherein one or more of the heteroatoms is selected from oxygen, nitrogen, or sulfur; heterocycloalkyl wherein the alkyl moiety comprises from 1 to 6 carbon atoms, and the heterocyclyl is as defined above; the substituent or substitutents relative to the above-named radicals are selected from the group consisting of amino, hydroxy, cyano, carboxyl, nitro, chloro, bromo, fluoro, alkoxy, mercapto, and alkylthio having from 1 to 6 carbon atoms, mercapto, perhaloalkyl having 1 to 3 carbon atoms, guanidino, amidino, and sulfamoyl atoms; and alkylthio having from 1 to 3 carbon atoms.

4. A compound according to claim 1 wherein $R^1$ and $R^2$ are independently selected from: hydrogen; substituted and unsubstituted: straight and branched loweralkyl having from 1 to 6 carbon atoms; cycloalkyl having from 3 to 6 carbon atoms, cycloalkylalkyl wherein the cycloalkyl moiety comprises 3 to 6 atoms and the alkyl moiety comprises 1 to 6 carbon atoms; phenyl, benzyl; wherein the substituent or substituents on the above-named radicals are selected from fluoro, hydroxy, mercapto, alkoxy having from 1 to 3 carbon atoms; and alkylthio having from 1 to 3 carbon atoms.

5. A compound according to claim 1 wherein the connecting group A is selected from: a single, direct bond; substituted and unsubstituted: alkyl having from 1 to 6 carbon atoms; cycloalkyl having from 3 to 10 atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; alkenyl having from 2 to 10 carbon atoms, cycloalkenyl having from 3 to 10 carbon atoms, cycloalkenylalkyl wherein the cycloalkenyl moiety comprises 3 to 10 carbon atoms and the alkyl moiety comprises 1 to 6 carbon atoms; alkynyl having from 2 to 10 carbon atoms; phenyl; naphthyl; arylalkyl and alkylaryl wherein aryl is phenyl and the alkyl has 1 to 6 carbon atoms; heteroalkyl, alkylheteroalkyl, arylheteroalkyl and alkylheteroaryl wherein the heteroatom or atoms are selected from the group of sulfur, oxygen and nitrogen, the alkyl moiety has 1 to 6 carbon atoms, and the aryl moiety is phenyl; heterocyclyl (saturated and unsaturated) comprising mono- and bicyclic structures having 3 to 10 ring atoms wherein one or more of the heteroatoms is selected from oxygen, nitrogen, or sulphur; heterocyclylalkyl wherein heterocyclyl moiety comprises from 3 to 10 atoms and the alkyl moiety comprises from 1 to 6 atoms; the substituent or substituents relative to the above-named radicals are selected from the group consisting of amino, hydroxyl, cyano, carboxyl, nitro, chloro, bromo, fluoro, alkoxy having from 1 to 6 carbon atoms, mercapto, perhaloalkyl and alkylthio having from 1 to 6 carbon atoms.

6. A compound according to claim 1 wherein the connecting group A is selected from: a single, direct bond, substituted and unsubstituted: straight and branched loweralkyl having from 1 to 6 carbon atoms, cycloalkyl having from 3 to 6 carbon atoms; phenyl; heterocyclyl selected from: thiophene, imidazole, pyridine, tetrazole and furane; alkylheteroakyl wherein the alkyl moiety comprises 1 to 3 carbon atoms and the heteroatom or atoms are sulfur, oxygen and nitrogen; the substituents relative to the above-named radicals are: amino, hydroxyl, chloro, bromo, fluoro, cyano, carboxyl, alkoxy having from 1 to 3 carbon atoms, mercapto, trifluoromethyl, and alkylthio having from 1 to 3 carbon atoms.

7. A compound according to claim 1 wherein $—SR^8$ is selected from the group consisting of:

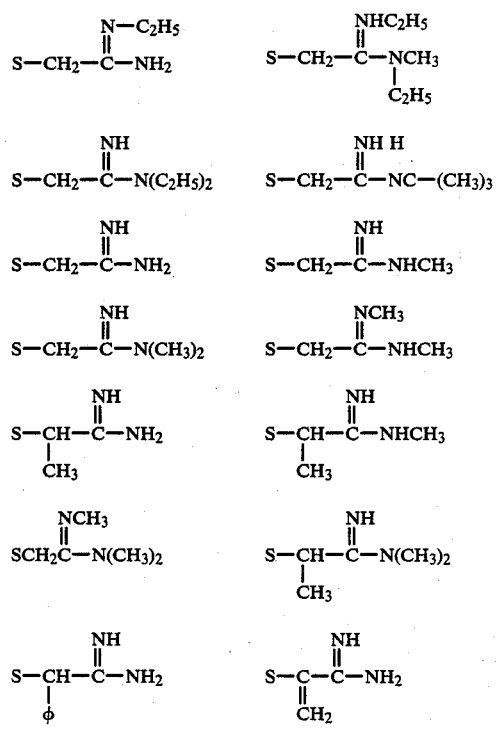

-continued
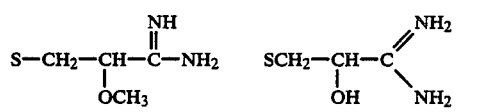
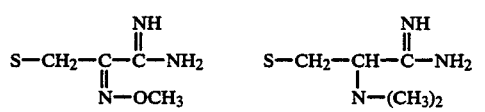
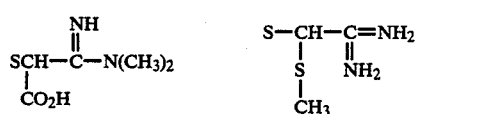
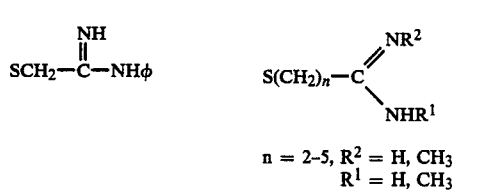
n = 2-5, R² = H, CH₃
R¹ = H, CH₃
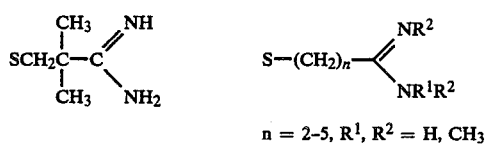
n = 2-5, R¹, R² = H, CH₃
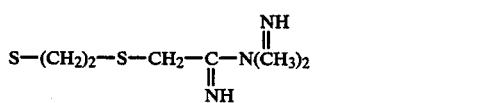
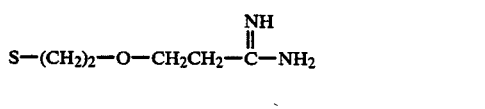
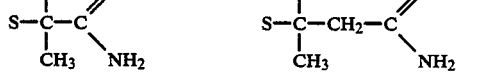
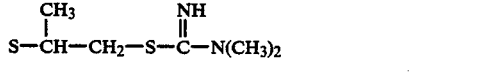
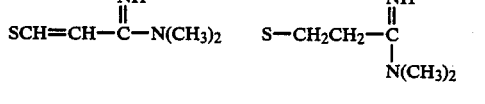
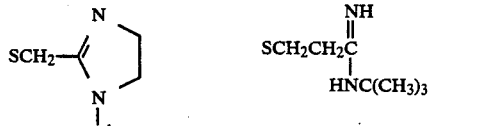
R₁ = H, CH₃
-continued
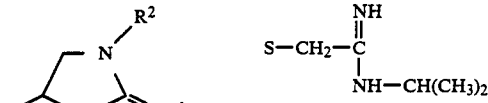
R¹ = H, CH₃
R² = H, CH₃
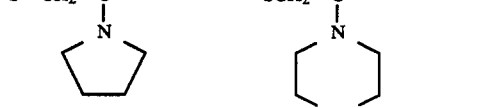
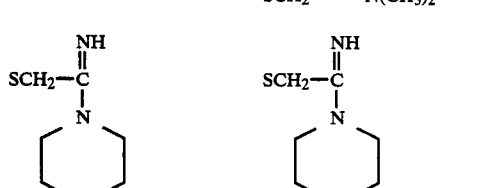
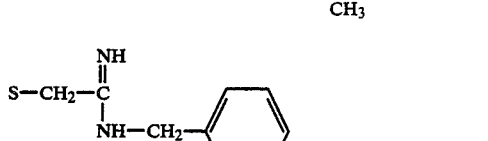
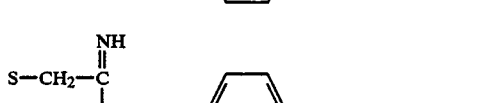
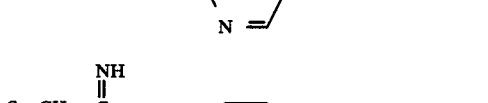
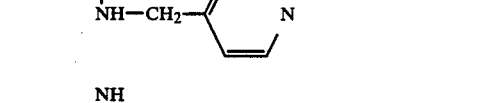
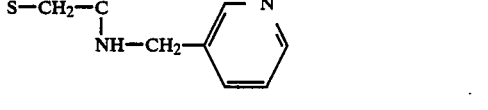
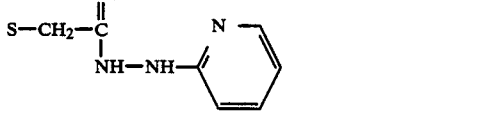
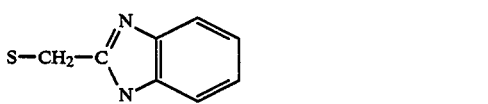

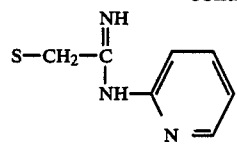
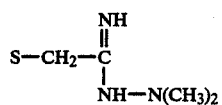
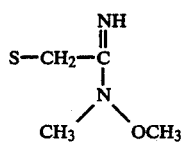
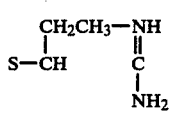
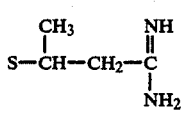
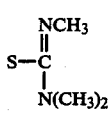
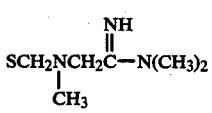
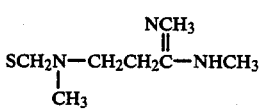
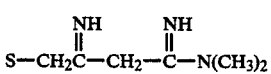
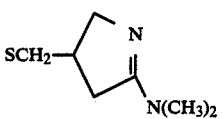
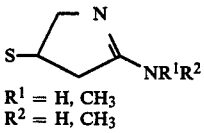
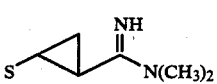
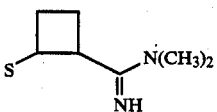
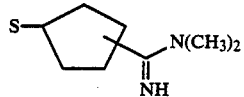
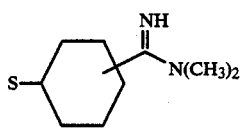
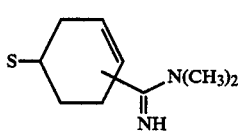
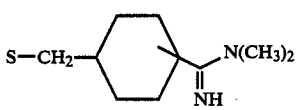
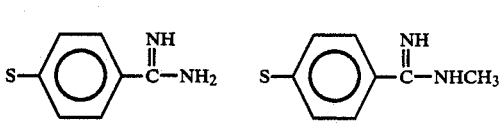
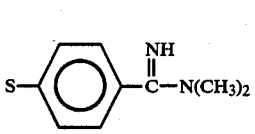
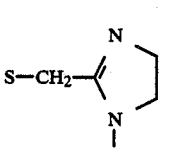
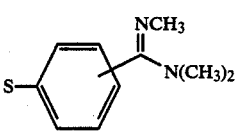
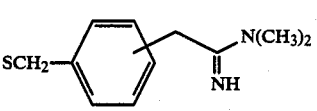
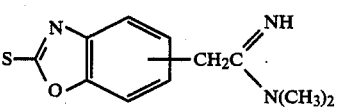
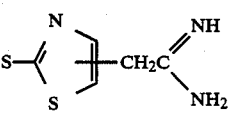
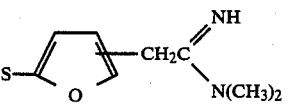

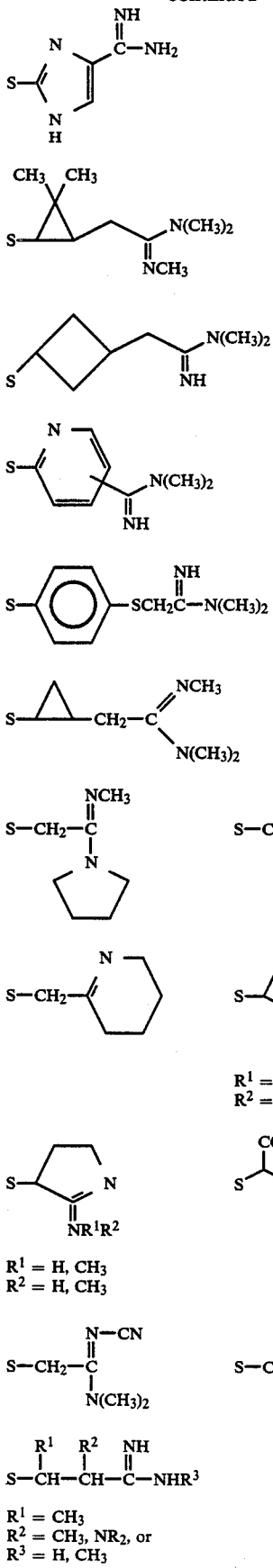

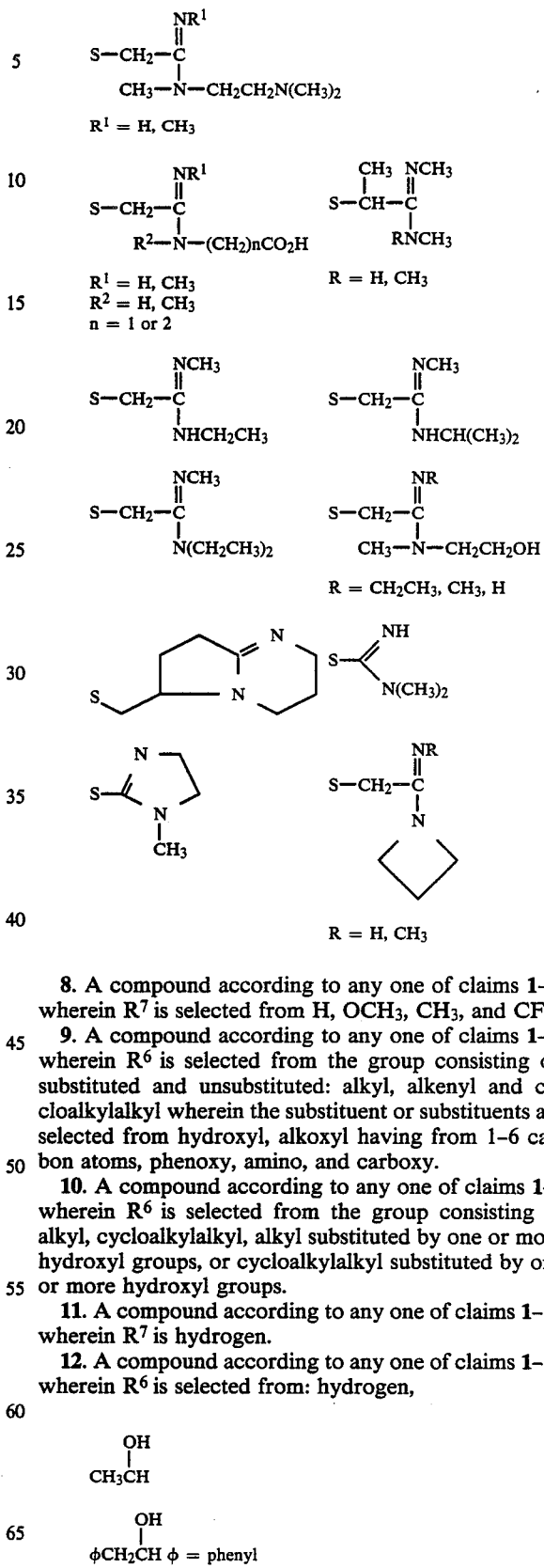

8. A compound according to any one of claims 1–7, wherein $R^7$ is selected from H, $OCH_3$, $CH_3$, and $CF_3$.

9. A compound according to any one of claims 1–8, wherein $R^6$ is selected from the group consisting of: substituted and unsubstituted: alkyl, alkenyl and cycloalkylalkyl wherein the substituent or substituents are selected from hydroxyl, alkoxyl having from 1–6 carbon atoms, phenoxy, amino, and carboxy.

10. A compound according to any one of claims 1–9 wherein $R^6$ is selected from the group consisting of alkyl, cycloalkylalkyl, alkyl substituted by one or more hydroxyl groups, or cycloalkylalkyl substituted by one or more hydroxyl groups.

11. A compound according to any one of claims 1–10 wherein $R^7$ is hydrogen.

12. A compound according to any one of claims 1–11 wherein $R^6$ is selected from: hydrogen, $$CH_3\overset{OH}{\underset{|}{CH}}$$

$$\phi CH_2\overset{OH}{\underset{|}{CH}} \quad \phi = phenyl$$

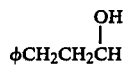
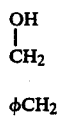
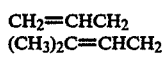
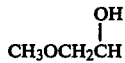
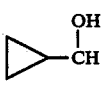
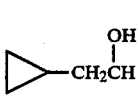
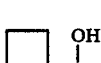
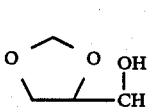
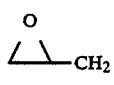
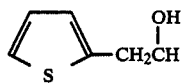
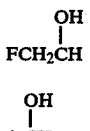
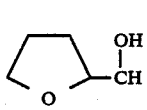
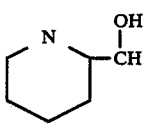
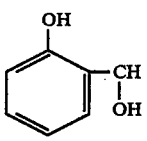
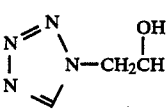
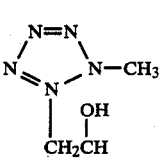
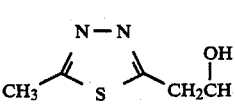
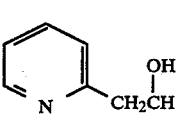
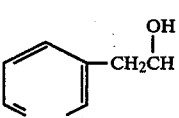
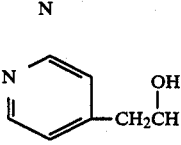

-continued

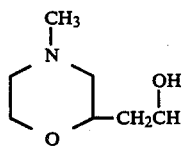

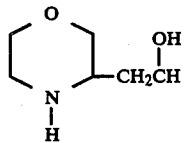

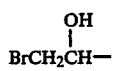

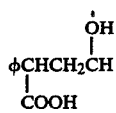

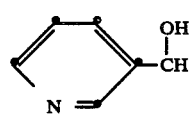

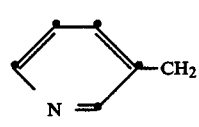

CH₃CF₂

CH₃O

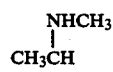

CH₃O₂C
NH₂CO
CH₃NHCO

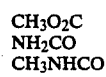

CF₃

-continued

CH₂=CH
CH≡C
H₂NCH₂
F₂CHCH₂
CH₂=
(HOCH₂)(CH₃)C=

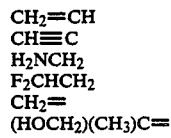

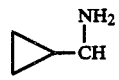

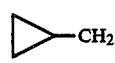

CH₃O₂CCH₂, F, OH.

13. A compound according to any one of claims 1–12, wherein R⁶ is hydrogen,

CH₃CH₂

FCH₂CH(OH)
(CH₃)₂C(OH)

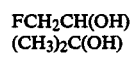

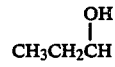

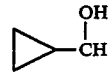

HOCH₂
HO₂CCH₂

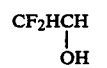

CH₃O
(CH₃)₂CH
CF₃, CF₃CH₂

14. A compound according to claim 1 wherein: R⁷ is hydrogen, hydroxyl, alkoxyl, alkylthio, mercapto, chloro, fluoro, bromo, alkyl and substituted alkyl wherein the substituent or substituents are: alkoxyl, hydroxyl, fluoro, amino, and mercapto.

15. A compound according to claim 1 wherein R⁷ is hydrogen, hydroxyl, OCH₃, CH₃, hydroxyl and polyhydroxyl-substituted alkyl.

16. A compound according to claim 1 wherein R⁷ is hydrogen, CH₃, OCH₃, or CF₃.

17. A compound according to any one of claims 1-16 wherein $R^6$ is: hydrogen; substituted and unsubstituted: alkyl, cycloalkyl, cycloalkylalkyl, phenylalkyl; wherein the substituent or substituents are selected from: hydroxyl, chloro, fluoro, bromo, carboxyl, oximino, alkoximino, ureido, amino, alkoxyl, or alkylthio.

18. A compound according to claim 17 wherein the substituent or substituents on $R^6$ are hydroxyl.

19. A compound according to claim 1 wherein $R^7$ is hydrogen, hydroxyl, alkoxyl, alkylthio, chloro, fluoro, bromo, alkyl and substituted alkyl wherein the substituent or substituents are: alkoxyl, hydroxyl, or fluoro; and $R^6$ is: hydrogen; substituted and unsubstituted: alkyl, cycloalkyl, cycloalkylalkyl, phenylalkyl; wherein the substituent or substituents are selected from: hydroxyl, chloro, fluoro, bromo, oximino, alkoximino, ureido, amino, alkoxyl, alkylthio, or mercapto.

20. A compound according to claim 1 wherein $R^7$ is hydrogen, hydroxyl, alkoxyl, alkylthio, mercapto, chloro, fluoro, bromo, alkyl and substituted alkyl wherein the substituent or substituents are: alkoxyl, hydroxyl, or fluoro; and $R^6$ is hydrogen; substituted and unsubstituted: alkyl, cycloalkyl, cycloallkylalkyl, phenylalkyl; wherein the substituent or substituents are selected from: hydroxyl, chloro, fluoro, bromo, oximino, alkoximino, ureido, amino, alkoxyl, alkylthio, or mercapto.

21. A compound according to any one of claim 1-20 wherein $R^7$ is hydrogen, $CH_3$ or $OCH_3$.

22. A compound according to claim 21 wherein $R^6$ is selected from:

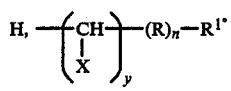

wherein:
y=0 or 1;
X=OH, $NH_2$; SH;
n=0 or 1;
R=substituted or unsubstituted: alkyl, alkenyl or alkynyl having 1-6 carbon atoms wherein the substituent is $R^{1°}$; $R^{1°}$=alkoxyl, carboxyl, $CF_3$, OH, H, linear or branched alkyl bearing 1 or more hydroxyl groups, amino, aminoalkyl, Cl, F, Br, alkylthio, amidino, guanidino, oximino, phenyloxy, phenylthio,

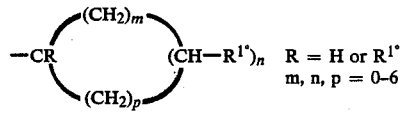  R = H or $R^{1°}$
m, n, p = 0-6

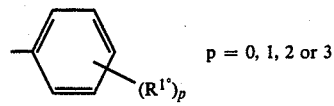  p = 0, 1, 2 or 3

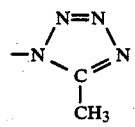

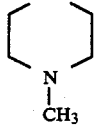

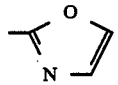

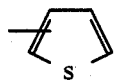

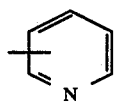

23. A compound according to any one of claims 1-22 wherein $R^6$ is selected from:

—H
—$CH_2OH$
—$CH(OH)CH_3$
—$CH_2CH_2OH$
—$CH(OH)CH(CH_3)_2$
—$CH(OH)CH_2CH(CH_3)_2$
—$CH_2CH_2CH_2OH$
—$CH_2CH_2CH_2CH_2OH$
—$CH(OH)CH_2CH_2OH$

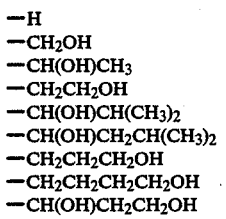

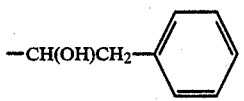

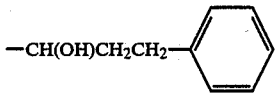

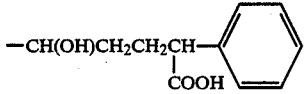

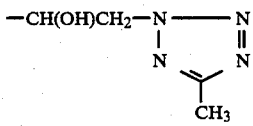

-continued
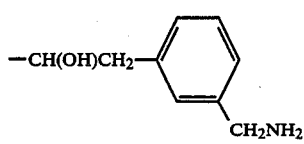
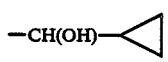
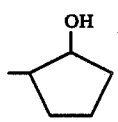
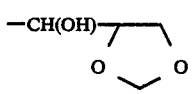
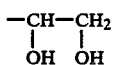
-continued
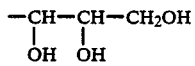
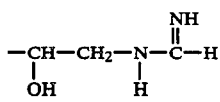
-CH(OH)CH₂CH₃
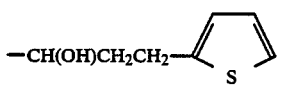
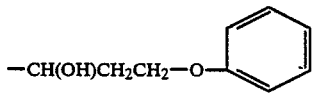
24. A method of treatment comprising administering an antibacterially effective amount of a compound according to claim 1.
25. An antibiotic composition comprising a therapeutically effective amount of a compound according to claim 1 and a pharmaceutically effective carrier therefor.
* * * * *